US012004879B2

(12) United States Patent
Ferber et al.

(10) Patent No.: US 12,004,879 B2
(45) Date of Patent: Jun. 11, 2024

(54) SYSTEMS AND METHODS FOR DETECTING PHOTOPLETHYSMOGRAPHIC DEVICE USAGE

(71) Applicant: ITAMAR MEDICAL SPRY 2021, LIMITED PARTNERSHIP, Caesarea (IL)

(72) Inventors: Elad Ferber, Woodside, CA (US); Pierre-Jean Cobut, Menlo Park, CA (US); Ramkrishnan Narayanan, San Jose, CA (US); Derya Gol Gungor, Sunnyvale, CA (US)

(73) Assignee: Itamar Medical Spry 2021, Limited Partnership, Caesarea (IL)

( * ) Notice: Subject to any disclaimer, the term of this patent is extended or adjusted under 35 U.S.C. 154(b) by 159 days.

(21) Appl. No.: 17/648,498

(22) Filed: Jan. 20, 2022

(65) Prior Publication Data
US 2022/0142587 A1    May 12, 2022

Related U.S. Application Data

(63) Continuation of application No. 15/368,510, filed on Dec. 2, 2016, now Pat. No. 11,259,753.
(Continued)

(51) Int. Cl.
*A61B 5/05*     (2021.01)
*A61B 5/00*     (2006.01)
(Continued)

(52) U.S. Cl.
CPC .......... *A61B 5/7221* (2013.01); *A61B 5/0002* (2013.01); *A61B 5/0008* (2013.01);
(Continued)

(58) Field of Classification Search
CPC ... A61B 5/7221; A61B 5/0002; A61B 5/0008; A61B 5/0022; A61B 5/0064; A61B 5/0205; A61B 5/021
See application file for complete search history.

(56) References Cited

U.S. PATENT DOCUMENTS 5,309,916 A    5/1994  Hatschek
6,331,162 B1   12/2001 Mitchell
(Continued)

FOREIGN PATENT DOCUMENTS

EP    0467853 B1    1/1996
EP    1611847 A1    1/2006
(Continued)

OTHER PUBLICATIONS

Deshmane, Anagha Vishwas, "False Arrhythmia Alarm Suppression Using ECG, ABP, and Photoplethysmogram," Master's Thesis, Massachusetts Institute of Technology, Sep. 2009.
(Continued)

*Primary Examiner* — Joel F Brutus
(74) *Attorney, Agent, or Firm* — Itamar Medical Spry 2021, Limited Partnership

(57) ABSTRACT

Systems and methods for determining if a wearable photoplethysmography device is correctly positioned in operating to medical signs of a user by using a classifier to determine if a signal is valid or invalid. In some embodiments, in using the classifier to determine in a signal is valid or invalid, a lean method of linear computational complexity and minimal memory complexity is provided for determining at the wearable photoplethysmography device if it is correctly positioned. In some embodiments, in using the classifier minimal computational complexity is used in determining at the wearable photoplethysmography device if it is correctly positioned.

17 Claims, 11 Drawing Sheets

Related U.S. Application Data

(60) Provisional application No. 62/262,532, filed on Dec. 3, 2015, provisional application No. 62/262,540, filed on Dec. 3, 2015, provisional application No. 62/262,342, filed on Dec. 2, 2015.

(51) Int. Cl.

| | | |
|---|---|---|
| *A61B 5/0205* | (2006.01) | |
| *A61B 5/021* | (2006.01) | |
| *A61B 5/024* | (2006.01) | |
| *A61B 5/08* | (2006.01) | |
| *A61B 5/117* | (2016.01) | |
| *A61B 5/145* | (2006.01) | |
| *A61B 5/1455* | (2006.01) | |
| *G16H 40/67* | (2018.01) | |

(52) U.S. Cl.
CPC .......... *A61B 5/0022* (2013.01); *A61B 5/0064* (2013.01); *A61B 5/0205* (2013.01); *A61B 5/021* (2013.01); *A61B 5/02125* (2013.01); *A61B 5/02141* (2013.01); *A61B 5/024* (2013.01); *A61B 5/02416* (2013.01); *A61B 5/0806* (2013.01); *A61B 5/0816* (2013.01); *A61B 5/117* (2013.01); *A61B 5/14532* (2013.01); *A61B 5/14535* (2013.01); *A61B 5/14539* (2013.01); *A61B 5/14546* (2013.01); *A61B 5/1455* (2013.01); *A61B 5/14551* (2013.01); *A61B 5/4872* (2013.01); *A61B 5/6802* (2013.01); *A61B 5/6816* (2013.01); *A61B 5/6823* (2013.01); *A61B 5/6824* (2013.01); *A61B 5/6829* (2013.01); *A61B 5/7203* (2013.01); *A61B 5/721* (2013.01); *A61B 5/7264* (2013.01); *A61B 5/7267* (2013.01); *A61B 5/7275* (2013.01); *A61B 5/7278* (2013.01); *A61B 5/7435* (2013.01); *G16H 40/67* (2018.01)

(56) References Cited

U.S. PATENT DOCUMENTS

| | | |
|---|---|---|
| 6,616,613 B1 | 9/2003 | Goodman |
| 7,006,856 B2 | 2/2006 | Baker, Jr. et al. |
| 7,194,293 B2 | 3/2007 | Baker, Jr. |
| 7,539,532 B2 | 5/2009 | Tran |
| 7,621,876 B2 | 11/2009 | Hoctor et al. |
| 7,674,231 B2 | 3/2010 | McCombie et al. |
| 8,290,730 B2 | 10/2012 | Watson et al. |
| 8,430,817 B1 | 4/2013 | Al-Ali et al. |
| 8,478,403 B2 | 7/2013 | Wenzel et al. |
| 8,532,932 B2 | 9/2013 | McGonigle et al. |
| 8,888,700 B2 | 11/2014 | Banet et al. |
| 9,402,554 B2 | 8/2016 | Ochs et al. |
| 9,560,995 B2 | 2/2017 | Addison et al. |
| 9,706,964 B2 | 7/2017 | Ferber et al. |
| 10,765,331 B2 | 9/2020 | Morris et al. |
| 2003/0036685 A1 | 2/2003 | Goodman |
| 2004/0138540 A1 | 7/2004 | Baker et al. |
| 2006/0122476 A1 | 6/2006 | Slyke |
| 2006/0211942 A1 | 9/2006 | Hoctor et al. |
| 2008/0039731 A1 | 2/2008 | McCombie et al. |
| 2009/0326349 A1 | 12/2009 | McGonigle et al. |
| 2011/0257489 A1 | 10/2011 | Banet et al. |
| 2012/0029363 A1 | 2/2012 | Lund |
| 2012/0215275 A1 | 8/2012 | Wenzel et al. |
| 2013/0079657 A1 | 3/2013 | Ochs et al. |
| 2013/0197322 A1 | 8/2013 | Tran |
| 2014/0031652 A1 | 1/2014 | Baker, Jr. |
| 2014/0243633 A1 | 8/2014 | Addison et al. |
| 2014/0316226 A1 | 10/2014 | Ferber et al. |
| 2015/0065889 A1 | 3/2015 | Gandelman et al. |
| 2015/0313484 A1* | 11/2015 | Burg ................. A61B 5/021 600/534 |
| 2015/0351699 A1 | 12/2015 | Addison et al. |
| 2015/0359436 A1 | 12/2015 | Shim et al. |
| 2016/0029898 A1 | 2/2016 | LeBoeuf et al. |
| 2016/0094899 A1* | 3/2016 | Aumer ................. A61B 5/6802 340/870.07 |
| 2016/0242700 A1 | 8/2016 | Ferber et al. |
| 2016/0287110 A1 | 10/2016 | Morris et al. |
| 2016/0360984 A1* | 12/2016 | Albadawi ............. A61B 5/7246 |

FOREIGN PATENT DOCUMENTS

| | | |
|---|---|---|
| EP | 2448475 A1 | 5/2012 |
| WO | 2014153200 A1 | 9/2014 |
| WO | 2015107268 A1 | 7/2015 |
| WO | 2015116891 A1 | 8/2015 |

OTHER PUBLICATIONS

European Patent Application No. 16871673.6, Search Report dated Jun. 3, 2019.

European Patent Application No. 16871674.4, Search Report dated Jun. 3, 2019.

European Patent Application No. 16871678.5, Search Report dated Jun. 3, 2019.

International Application No. PCT/US2016/064843, International Search Report and Written Opinion mailed Apr. 3, 2017.

International Application No. PCT/US2016/064848, International Search Report and Written Opinion mailed Mar. 27, 2017.

International Application No. PCT/US2016064838, International Search Report and Written Opinion mailed Mar. 29, 2017.

Silva, Ikaro et al., "Signal Quality Estimation with Multichannel Adaptive Filtering in Intensive Care Settings," IEEE Transactions in Biomedical Engineering, vol. 59, No. 9, pp. 2476-2485, Sep. 2012.

* cited by examiner

SYSTEMS AND METHODS FOR DETECTING PHOTOPLETHYSMOGRAPHIC DEVICE USAGE

CROSS-REFERENCE TO RELATED APPLICATIONS

The present application is a continuation of U.S. patent application Ser. No. 15/368,510, filed Dec. 2, 2016, which claims the benefit of U.S. Provisional Patent Application Ser. No. 62/262,540, filed Dec. 3, 2015, entitled "Prediction of Blood Pressure from PPG Data," U.S. Provisional Patent Application Ser. No. 62/262,532, filed Dec. 3, 2015, entitled "Validity and Classification for Biological Signal Recognition," and U.S. Provisional Patent Application Ser. No. 62/262,342, filed Dec. 2, 2015, entitled "Respiratory Rate Estimation Using Multispectral Data," which are incorporated herein by reference.

BACKGROUND

Technical Field

Embodiments of the present inventions relate generally to photoplethysmography devices. More specifically, embodiments of the present inventions relate to validity of measurements made by photoplethysmography devices.

Description of Related Art

Wearable activity monitoring devices are growing in popularity. These devices are directed to facilitate monitor medical signs of a user to improve overall health. In particular, minimally invasive photoplethysmography devices have been developed to measure medical signs of users to improve overall health of the user. It is important that any such measurements are valid in order to improve overall health of the users. However, such devices are susceptible to being positioned incorrectly leading to the measuring medical signs being invalid. Further, signs measured by a current wearable activity monitoring devices are often processed even though the signs are invalid. As a result, these devices lead to wasted power consumption for no benefit.

Photoplethysmography devices have been implemented in wearable devices. Such devices are small to allow for easy wearing by a user and also lack computational resources. Due, to the lack of size and computational resources, there has been difficulty in implementing systems and methods at the photoplethysmography devices that allows for the photoplethysmography devices themselves to determine if they are positioned correctly.

SUMMARY

An example system may comprise a signal input module at a wearable photoplethysmography device. The signal input module may be configured to receive a signal from an energy receiver of the wearable photoplethysmography device. The signal may be generated by the energy receiver, at least in part, based upon a received portion of energy projected by an energy transmitter of the wearable photoplethysmography device operating to measure medical signs of a user.

The system may include a wave feature selection module configured to select a subset of wave features of a plurality of wave features of the signal received from the energy receiver. The system may comprise a wave metric calculation determination module configured to determine wave metric calculations of a set of wave metric calculations for the subset of wave features selected by the wave feature selection module. Additionally, the system may comprise a wave metric-based signal validity classification module configured to classify the signal by applying a validity classifier to at least one of the wave metric calculations to generate a validity score for the signal. In various embodiments, the validity classifier generated based on the set of wave metric calculations. The validity classifier may be used to determine if the wearable photoplethysmography device is correctly positioned in operating to measure the medical signs of the user.

The system may include a validity prediction module configured to compare the validity score to a validity threshold to determine if the wearable photoplethysmography device is correctly positioned in operating to measure the medical signs of the user based on application of the validity classifier to the at least one of the wave metric calculations. The system may include a signal validity-based device control module at the wearable photoplethysmography device configured to control operation of the wearable photoplethysmography device based on whether it is determined the wearable photoplethysmography device is correctly positioned in operating to measure the medical signs of the user based on a comparison of the validity score to the validity threshold.

In some embodiments, the validity prediction module may be configured to determine the wearable photoplethysmography device is operating to measure the medical signs of the user based on the comparison of the validity score to the validity threshold.

In some embodiments, the signal validity-based device control module may be configured to cause the energy transmitter to stop operating in emitting energy for use by the wearable photoplethysmography device in operating to measure the medical signs of the user.

In some embodiments, the wave metric-based signal validity classification module may be configured to classify the signal by applying the validity classifier to the wave metric calculations of the set of wave metric calculations to generate a plurality of validity scores including the validity score for the signal;

In some embodiments, the example system includes a smoothing module configured to apply temporal smoothing to the plurality of validity scores for the signal to generate a smoothed validity score;

In some embodiments, the validity prediction module may be configured to compare the smoothed validity score to the to the validity threshold to determine if the wearable photoplethysmography device is correctly positioned in operating to measure the medical signs of the user;

In some embodiments, the signal validity-based device control module may be configured to control operation of the wearable photoplethysmography device based on whether it is determined the wearable photoplethysmography device is correctly positioned in operating to measure the medical signs of the user based on a comparison of the smoothed validity score to the validity threshold.

In some embodiments, the smoothing module may be configured to apply rank smoothing to the plurality of validity scores, the smoothed validity score selected from the plurality of validity scores based on the value of the smoothed validity score according to the rank smoothing.

In some embodiments, the wave feature selection module may be configured to normalize the signal before selecting the subset of wave features of the plurality of wave features of the signal.

An exemplary method may comprise receiving a signal from an energy receiver of a wearable photoplethysmography device. The signal may be generated by the energy receiver, at least in part, based upon a received portion of energy projected by an energy transmitter of the wearable photoplethysmography device operating to measure medical signs of a user. The method may further comprise selecting a subset of wave features of a plurality of wave features of the signal received from the energy receiver, determining wave metric calculations of a set of wave metric calculations for the subset of wave features selected from the signal, classifying the signal by applying a validity classifier to at least one of the wave metric calculations to generate a validity score for the signal, comparing the validity score to a validity threshold to determine if the wearable photoplethysmography device is correctly positioned in operating to measure the medical signs of the user, and controlling operation of the wearable photoplethysmography device based on whether it is determined the wearable photoplethysmography device is correctly positioned in operating to measure the medical signs of the user based on a comparison of the validity score to the validity threshold.

In some embodiments, the example method may include classifying the signal by applying the validity classifier to the wave metric calculations of the set of wave metric calculations to generate a plurality of validity scores including the validity score for the signal, applying temporal smoothing to the plurality of validity scores for the signal to generate a smoothed validity score, comparing the smoothed validity score to the to the validity threshold to determine if the wearable photoplethysmography device is correctly positioned in operating to measure the medical signs of the user, and controlling operation of the wearable photoplethysmography device based on whether it is determined the wearable photoplethysmography device is correctly positioned in operating to measure the medical signs of the user based on a comparison of the smoothed validity score to the validity threshold.

In some embodiments, the example method may include normalizing the signal before selecting the subset of wave features of the plurality of wave features of the signal.

In some embodiments, the wave metric calculations of the set of wave metric calculations to which the validity classifier is applied may include signal energy measurements of the signal determined from the subset of wave features.

In some embodiments, the wave metric calculations of the set of wave metric calculations to which the validity classifier is applied may include signal mobility measurements of the signal determined from the subset of wave features and the signal energy measurements of the signal determined from the subset of wave features.

In some embodiments, the wave metric calculations of the set of wave metric calculations to which the validity classifier is applied may include complexity measurements of the signal determined from the subset of wave features and the signal mobility of the measurements of the signal determined from the subset of wave features.

In some embodiments, the wave metric calculations of the set of wave metric calculation to which the validity classifier is applied may include one or a combination of signal crossing measurements of the signal and signal non-oscillatory component measurements of the signal determined from the subset of wave features.

In some embodiments, the validity classifier applied to the wave metric calculations may be generated from one or a combination of signal energy measurements, signal mobility measurements, signal complexity measurements, signal crossing measurements, and signal non-oscillatory component measurements of signals known to be valid or invalid by being generated by at least one wearable photoplethysmography device correctly positioned in operating to measure the medical signs and at least another wearable photoplethysmography device incorrectly positioned in operating to measure the medical signs.

In some embodiments, applying temporal smoothing may include applying rank smoothing to the plurality of validity scores and the smoothed validity score selected from the plurality of validity scores may be based on the value of the smoothed validity score according to the rank smoothing.

Other features and aspects of various embodiments will become apparent from the following detailed description, taken in conjunction with the accompanying drawings, which illustrate, by way of example, the features of such embodiments.

DETAILED DESCRIPTION

Figure 1:
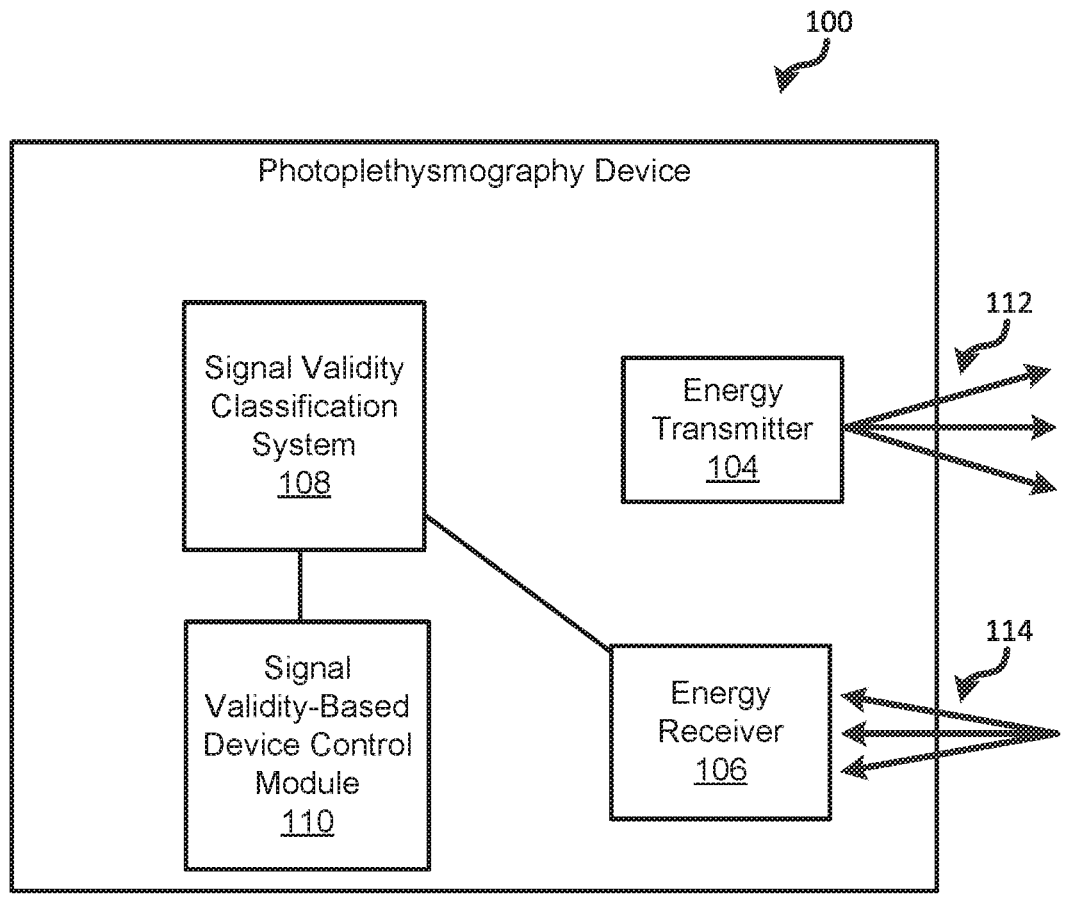
FIG. 1 is a block diagram illustrating an example photoplethysmography device.

Medical signs including blood metrics may be measured by minimally invasive procedures to discover diseases, diagnose diseases, or address medical conditions. Minimal-invasive procedure based devices may have the advantages of reducing costs and decreasing the need for invasive methods, thereby increasing the comfort and well-being of users and patients. Even though these devices have revolutionized patient care, they have only been approved for medical purposes. Minimal-invasive procedure based devices are usually out of reach for the general public because they are designed for medical purposes rather than non-medical purposes such as fitness, well-being, and quality of life.

For example, personal devices such as sphygmomanometers or pulse oximeters measure blood pressure or oxygen levels, respectively, on a per-request basis. They usually do not measure blood metrics in real time or periodically. Real-time blood metrics data (e.g., high resolution measurements or measurements over long periods of time) may allow users monitoring and controlling their energy levels and/or metabolism. Nutritionists, people suffering from obesity, people desiring to eat healthier, fitness enthusiasts, semi-professional athletes, people likely to have hypoglycemia, and/or the general population may benefit from these devices.

In various embodiments, a wearable photoplethysmography device measures medical signs of users. The photoplethysmography device may measure any number of applicable medical signs including, for example, respiration rates, depth of anesthesia, hypovolemia, and hypervolemia. The photoplethysmography device may monitor, store, track, communicate, and/or analyze medical signs of a user.

In various embodiments, the wearable photoplethysmography device may be or include a multispectral blood metric measurement apparatus that monitors blood metrics, fitness, and/or metabolism levels of various users in a non-invasive manner. The multispectral blood metric measurement apparatus may measure any number of blood metrics which may include, for example, various nutrient blood concentrations.

Wearable photoplethysmography devices need to be positioned correctly with respect to a user to accurately determine the user's medical signs. Incorrectly positioned wearable photoplethysmography devices includes those wearable photoplethysmography devices that are positioned improperly on the user (e.g., the wearer) or are not worn at all. While an incorrectly positioned wearable photoplethysmography device may still function to generate and detect optical signals, any measurements based on those detected optical signals will be invalid. For example, if the wearable photoplethysmography device is not positioned on the user correctly, the photoplethysmography device may receive optical signals with too much noise, interference, and/or distortion. Invalid signals (e.g., signals with too much noise, interference, and/or distortion) may lead to erroneous measurements of medical signs. In another example, if the user is not wearing the wearable photoplethysmography device at all, any detected signals by the wearable photoplethysmography device will be invalid for evaluating medical signs of the user.

Invalid signals (e.g., caused by a user not wearing the wearable photoplethysmography device or not positioning the wearable photoplethysmography device correctly) lead to a waste by consuming computational resources in calculating measurements of medical signs that are ultimately worthless or otherwise erroneous.

Previous attempts have been made to determine whether photoplethysmography devices are correctly positioned to operate in measuring medical signs. For examples, sensors have been incorporated into photoplethysmography devices for use in determining whether the photoplethysmography devices are correctly positioned to measure medical signs of a user. Incorporating other sensors into photoplethysmography devices to determine whether the photoplethysmography devices are correctly positioned have, in the past, increased the size of the apparatuses and increased the cost of the apparatuses.

A photoplethysmography device may be determined to be correctly positioned based on energy transmitted between energy transmitter and receiver of the photoplethysmography device. For example, signals based on energy transmitted between an energy transmitter and a receiver may be compared to historical data to detect invalid windows using physiological parameter estimates. Such approaches may consume considerable computational resources. The consumption of resources is critical when the photoplethysmography devices are implemented as wearable devices with limited processing power and data storage space. For example, approaches using comparisons of signals to historical data require signal warping and comparisons which may consume considerable computational resources. Additionally, such approaches do not account for differences between wearers and differences in medical situations for which medical signs are determined using a photoplethysmography device. For example, approaches using comparisons of signals to historical data do not account for differences in characteristics between different users, while approaches using invalid window detection uses bounds on physiological parameters that are exceeded in certain medical situations.

FIG. 1 is a block diagram illustrating an example photoplethysmography device 100. The photoplethysmography device 100 comprises an energy transmitter 104, an energy receiver 106, a signal validity classification system 108, and a signal validity-based device control module 110. In various embodiments, the photoplethysmography device 100 may be implemented as a wearable member. The wearable member may include, for example, a bracelet, glasses, necklace, ring, anklet, belt, broach, jewelry, clothing, or any other member or combination of members that allow the photoplethysmography device 100 to be close to or touch a body of the wearer to measure medical signs. In various embodiments, the photoplethysmography device 100 may be correctly positioned or incorrectly positioned to measure medical signs of a user. For example, the photoplethysmography device 100 may be not on the user's body at all or placed incorrectly (e.g., askew) such that signal measurement will lead to inaccurate results.

The energy transmitter 104 and the energy receiver 106 may be positioned on the photoplethysmography device 100 such that the energy transmitter 104 and the energy receiver 106 make contact or are proximate to tissue (e.g., skin) of a user. The signal validity classification system 108 and the signal validity-based device control module 110 may be coupled to the energy transmitter 104 and the energy receiver 106. The signal validity classification system 108 may be coupled to the energy transmitter 104 and the energy receiver 106.

The photoplethysmography device 100 may comprise a communication module (not shown) and/or an analyzer (not shown). The analyzer may be coupled to the energy receiver 106, the signal validity classification system 108, and/or the signal validity-based device control module 110. The communication module may be coupled to the energy receiver 106, the signal validity classification system 108, and/or the signal validity-based device control module 110.

The photoplethysmography device 100 may further comprise a driver (not shown) and a power source (not shown). The driver may be coupled to one or a combination of the energy transmitter 104, the energy receiver 106, the signal validity classification system 108, and the signal validity-based device control module 110. Similarly, the power source (e.g., a battery, capacitor, or other power supply) may supply power to the energy transmitter 104, the energy receiver 106, the signal validity classification system 108, and/or the signal validity-based device control module 110 via the driver.

In some embodiments, the photoplethysmography device 100 comprises an Analog-to-Digital Converter ("ADC") (not shown). The ADC may be coupled to the signal validity classification system 108 and the signal validity-based device control module 110.

In various embodiments, the energy transmitter 104 emits energy 112 including, but not limited to, light (e.g., optical beam(s) or optical signal(s)). For example, the energy transmitter 104 may emit energy 112 into the body (e.g., tissues) of the user, when the photoplethysmography device 100 is being worn by the user. The energy 112 emitted by the energy transmitter 104 may be in the direction of the user's tissues. The energy transmitter 104 may emit energy 112 or light at different wavelengths. The energy transmitter 104 may comprise any number of light emission diodes ("LEDs") or other energy sources. While LEDs are discussed herein for energy transmission, it will be appreciated that the energy transmitter 104 may include any number and any kind of energy sources (e.g., light sources).

In one example, the energy transmitter 104 comprises at least two LEDs. Each LED may be configured to emit energy 112 at one or more wavelengths. Each LED may emit light with a peak wavelength centered around a wavelength. For example, the energy transmitter 104 may emit light with a peak wavelength centered between 500 nm to 1800 nm. Further, in the example, the energy transmitter 104 may emit different wavelengths of light centered around at least one of 523 nm, 590 nm, 623 nm, 660 nm, 740 nm, 850 nm, and 940 nm. In another example, the energy transmitter 104 may emit light with a wavelength within the infrared spectrum.

Wavelengths of light emitted by the energy transmitter 104 may correspond to one or more metrics of medical signs to be measured. For example, wavelengths of light emitted by the energy transmitter 104 may correspond to one or more blood metrics of interest and/or one or more nutrients. Different components of the blood and/or different nutrients may absorb energy at different wavelengths. In various embodiments, a controller, driver, analyzer, or the like may assess or analyze metrics of medical signs being measured or estimated (e.g., of a user of the photoplethysmography device 100 and/or a user device not shown). The analyzer may determine metrics of medical signs from signals generated by the energy receiver 106 based on the receive energy 106 (e.g., the energy receiver 106 may generate a signal when energy is detected or otherwise received).

The controller, driver, analyzer or the like may associate medical signs to be measured with one or more wavelengths and configure one or more of the LEDs to emit energy 112 of at least one of the one or more wavelengths. For example, an analyzer may command the driver to deliver electric power to an LED that is configured to emit light at a desired wavelength.

In some embodiments, a number of wavelengths generated by the energy transmitter 104 are the number of blood components or molecules to be measured plus one. For example, when a total number of five (5) blood components and/or molecules are to be measured, a total number of six (6) wavelengths may be determined based on the blood components and/or molecules to be measured. One or more wavelengths may be associated with a nutrient or a combination of nutrients. In some embodiments, a number of wavelengths generated by the energy transmitter 104 are the number of nutrients to be measured plus one. For example, when a total number of three (3) nutrients are to be measured, a total number of four (4) wavelengths may be determined based on the nutrients to be measured.

The energy transmitter 104 may be configured to generate energy at a set of wavelengths. The energy transmitter 104 may be configured to generate energy such that energy at different wavelengths is generated sequentially and/or periodically. A period of time for the energy transmitter 104 to generate energy at each and every wavelength to be generated is a generation period. Subsequent to completion of the generation period, the energy transmitter 104 may start a new generation period thereby allowing multiple measurements. A generation period may be predetermined. For example, in a predetermined generation period, energy at all desired wavelengths may be generated by the energy transmitter 104.

In some embodiments, for each wavelength, the corresponding energy may be generated for a time period equal to a predetermined time duration divided by the number of wavelengths. For example, four (4) wavelengths may be determined and the predetermined time duration (e.g., generation period) is two (2) seconds. Accordingly, energy for each wavelength may be generated for a duration of half (0.5) second.

The energy receiver 106 may detect energy 114 associated with energy 112 provided by the energy transmitter 104. For example, the energy receiver 106 may detect at least a portion of the energy 112 emitted by the energy transmitter 104 through or reflected from within tissues (e.g., skin) of the user wearing the photoplethysmography device 100, regardless of whether the photoplethysmography device 100 is properly positioned. In various embodiments, the energy receiver 106 may detect energy 114 from the body of the user that is a fraction of the energy 112 produced by the energy transmitter 104. The energy receiver 106 may detect energy 112, at least a portion of which is energy 112 emitted by the energy transmitter that does not pass through or is otherwise directed at tissue of the user of the photoplethysmography device 100. For example, the energy receiver 106 may detect energy 114, at least a portion of which is directly transmitted from the energy transmitter as part of the emitted energy 112 without passing through tissue of a user, when the user is not wearing the photoplethysmography device 100.

The energy transmitter 104 and the energy receiver 106 may be configured such that the energy receiver 106 detects reflected energy from tissues of the user of the photoplethysmography device 100. For example, the energy transmitter 104 and the energy receiver 106 may be configured to be disposed on a surface or side of a user's tissues. The energy transmitter 104 and the energy receiver 106 may be configured such that the energy receiver 106 detects energy 114 based on reflected energy 112 initially emitted from the energy transmitter 104 that passed through or reflected from the user's tissues. In some embodiments, the energy transmitter 104 and the energy receiver 106 may be configured to be disposed on different (e.g., opposite) surfaces or sides of a user's tissues.

Energy 114 detected from tissues of a user may be detected by the energy receiver 106. The energy receiver 106 may be configured to generate a signal in response to detected energy 114. In some embodiments, the energy receiver 106 may generate different signals or signals with different information depending on the energy (e.g., wavelength) received. The energy receiver 106 may generate an output (e.g., signal(s)) that depends or partially depends upon the amount of energy 114 received. The energy receiver 106 may be configured to generate a signal (e.g., an electric current, or an electric voltage) in response to the energy 114 received from or through the user's tissues.

The signal(s) generated by the energy receiver 106 may be associated with one or more medical sign metrics. For example, a signal generated by the energy receiver 106 may be associated with one or more blood metrics and/or nutrients of interest. Energy at different wavelengths may be absorbed at a different rate (e.g., the rate may be related to a user's body state). The user's body state (e.g., heart rate, blood pressure, nutrient level, or the like) may determine the amount of energy absorbed by the body. Accordingly, energy reflected from or passed through the user's body at different wavelengths may be detected at different levels thereby causing different responses of the energy receiver 106. The energy receiver 106 may, for example, output signals based on the level of the energy 114 received.

The energy receiver 106 may provide information (e.g., within the signal) associated with the user's body state. For example, blood metric information may be determined (e.g., by an analyzer) from the output signal of the energy receiver 106.

The energy receiver 106 may comprise a set of photodetectors (e.g., a photo diode, or a photo transistor) which may be configured to output one or more signal(s) dependent upon photons or the like of received energy 114 based at least in part on energy emitted from the energy transmitter 104 that passed through tissues of the user. In various embodiments, the output signal of the energy receiver 106 is a composite of multiple signals. Each signal of the composite may be associated with energy at a wavelength which may be a portion (or fraction) of the total energy 112 emitted by the energy transmitter 104.

In various embodiments, the signal validity classification system 108 may determine a validity of one or more signal(s) generated by the energy receiver 106 in response to the received energy 114. Validity of a signal may indicate whether or not the signal was obtained when the photoplethysmography device 100 is correctly positioned to measure medical signs of a user. Whether the photoplethysmography device 100 is correctly positioned to measure medical signs of a user may include whether the user is actually wearing the photoplethysmography device 100 when the photoplethysmography device 100 is in operation (e.g., when the photoplethysmography device 100 is emitting and detecting energy). Additionally, whether the photoplethysmography device 100 is correctly positioned may include whether the user wearing the photoplethysmography device 100 has properly positioned the photoplethysmography device 100 to accurately measure medical signs. If it is determined that the photoplethysmography device 100 is incorrectly positioned (e.g. the user is not wearing the device at all or the user is wearing the device but it is not correctly positioned) then it may be determined that signals generated at the photoplethysmography device 100 are invalid.

The signal validity classification system 108 may be implemented at the photoplethysmography device 100 itself and may allow for the photoplethysmography device 100 to self-determine (e.g. without the use of external systems) whether signals generated by the energy receiver 106 based on the received energy 114 are valid.

In various embodiments, the signal validity classification system 108 determines a validity of a signal by classifying the signal using a validity classifier to calculate a validity score for the signal. The validity classifier may be applied to one or a plurality of wave metric calculations of a set of wave metric calculations derived from the signal. Wave metric calculations include applicable measurements, descriptors, and detectors which may be calculated from a signal or otherwise features of a signal (e.g., one or more waves of the signal). Example wave metric calculations include, but is not limited to, iSQI, bSQI, kSQI (Li), Hjorth Parameters (Deshmane, Oh), Interquartile Ratio or Perfusion, Energy, Zero-crossing Rate (Monte), template fit measures (Gaussian, Dynamic Time Warp, Longest Common Subsequence) (Li, Gartheeban), statistics of Kaiser Teager Energy (Mean, Variance, interquartile ratio, Skew) (Monte), Spectrum Template Matches, Spectral Entropy (Monte), characteristics determined according to Derivative-of-Gaussian filtering methods, periodicity measures, channel similarity measures, and characteristics determined according Wavelet-based detection methods.

In applying one or a plurality of wave metric calculations (e.g. five metric calculations), complexity and computation costs of determining signal validity is decreased. This may be beneficial as the signal validity classification system 108 is implemented at the photoplethysmography device 100 which, in some embodiments, when the photoplethysmography device 100 is a wearable device, processing power and memory is limited.

For example, in some embodiments, the wearable photoplethysmography device 100 may be able to determine if the signal is valid by using one or more tests. If the wearable photoplethysmography device 100 determines that the signal is invalid, the photoplethysmography device 100 may terminate any additional light emissions, detections, measurements, analysis, and/or the like. If the photoplethysmography device 100 determines that the signal is valid, the photoplethysmography device 100 may continue to perform additional actions (e.g., emit, detect, measure, analyze, and/or the like). As a result, computational resources and power may be saved by performing a limited number of tests regarding signal validity rather than performing measurements and analysis for assessment of the received signal(s).

In various embodiments, the validity classifier, used by the signal validity classification system 108, is generated based on wave metric calculations of a set of wave metric calculations made from previous signals generated at a plurality of photoplethysmography devices 100. For example, machine learning algorithms may be applied to known valid signals and known invalid signals to build the validity classifier based on wave metric calculations of the set of wave metric calculations of both known valid signals and known invalid signals. The validity classifier may include values, range of values, or functions of wave metric calculations of the set of wave metric calculations. For example, the validity classifier may include a range of values of a wave metric calculation indicating a signal is valid. The creation of the validity classifier is discussed herein.

In various embodiments, the validity classifier may be specific to characteristics of a user of the photoplethysmography device 100. For example, the validity classifier may be created based on wave metric calculations determined from signals received from photoplethysmography devices worn by users with one or more shared characteristics of the user (e.g., weight, height, health conditions, or the like). In various embodiments, the validity classifier used by the signal validity classification system 108 may be specific to a photoplethysmography device type. For example, the validity classifier may be created based on wave metric calculations determined form signals received from the photoplethysmography devices of the specific device type.

In various embodiments, the signal validity classification system 108 may generate a validity score for a signal based on application of the validity classifier to one or a plurality of wave metric calculations of the set of wave metric calculations of the signal. For example, the signal validity classification system 108 may apply the validity classifier to determined wave metric calculations of signal oscillatory energy from a single generated by the energy receiver 106 in response to the received energy 114 for purposes of determining whether the signal is valid. In another example, the signal validity classification system 108 may apply the validity classifier to determine a wave metric calculation of a comparison of oscillatory energy with its derivative from a signal generated by the energy receiver 106 for purposes of determining whether the signal is valid.

In various embodiments, the signal validity classification system 108 may compare the validity score to a validity threshold to determine if one or more signals are valid, and subsequently whether the user is correctly wearing the photoplethysmography device 100. For example, the signal validity classification system 108 may compare the validity score to a validity threshold to determine whether the user is wearing the photoplethysmography device 100 at all or whether the user is wearing the photoplethysmography device 100 and the device is correctly positioned. The validity threshold may be a validity score or a range of validity scores. In various embodiments, the signal validity classification system 108 may determine the signal is valid, corresponding to correct wearing of the photoplethysmography device 100 by the user, if the validity score falls at or above the validity threshold. Alternately, in various embodiments, the signal validity classification system 108 may determine the signal is valid, corresponding to correct wearing of the photoplethysmography device 100 by the user, if the validity score falls at or below the validity threshold.

The validity threshold is pre-set or selected. For example, the validity threshold may be pre-set or selected to achieve a specific number of true positive results for determining signal validity. In various embodiments, the validity threshold is pre-set or selected based on one or a combination of a device type of the photoplethysmography device 100, medical signs being measured by the photoplethysmography device 100, characteristics of a user of the photoplethysmography device 100, and/or a desired rate of achieving true positive results. For example, if the photoplethysmography device 100 is used to measure respiration rates in an overweight male, then the validity threshold of the validity classifier may be set to achieve a specific number of true positive results in measuring respiration rates in overweight males.

In some embodiments, the user may identify health concerns or health state information (e.g., weight), and/or demographic information regarding the user. The user may identify the information using the photoplethysmography device 100, an application (e.g., an app on a smartphone or personal computer) in communication with the photoplethysmography device 100, or a website. The photoplethysmography device 100, application, or website may then provide one or more identifiers that identify one or more validity thresholds (e.g., a subset of validity thresholds from a set of validity thresholds) associated with the provided information to the photoplethysmography device 100 which may then utilize the identified one or more validity thresholds. In some embodiments, the application or website may provide the subset of validity thresholds associated with the information provided by the user.

In various embodiments, the signal validity-based device control module 110 may control operation of the photoplethysmography device 100 based on a determination made by the signal validity classification system 108. The signal validity-based device control module 110 may control operation of any of the energy transmitter 104, the energy receiver 106, the signal validity classification system 108, the communication module, the driver, the power source, and/or the analyzer based on the determination of whether the photoplethysmography device 100 is correctly positioned. For example, if it is determined the signal or a plurality of signals in succession are invalid, indicating the photoplethysmography device 100 is incorrectly positioned, then the signal validity-based device control module 110 may instruct, or otherwise cause, any of the energy transmitter 104, the energy receiver 106, the signal validity classification system 108, the communication module, the driver, the power source, and/or the analyzer to stop operation before further analysis is performed, operate in a reduced capacity, deactivate one or more components of the photoplethysmography device 100, or operate to consume a reduced amount of power.

In various embodiments, the signal validity-based device control module 110 may control operation of the photoplethysmography device 100 based on a determination of whether the photoplethysmography device 100 is properly positioned using the communication module. For example, the signal validity-based device control module 110 may instruct the communication module to send status updates to a remote system, indicating whether the user is correctly wearing the photoplethysmography device 100 based on a determination of whether the photoplethysmography device 100 is correctly positioned.

The signal validity-based device control module 110 may receive instructions regarding controlling operation of the photoplethysmography device 100 from a remote system based on a determination made by the signal validity classification system 108 regarding validity of one or a plurality of signals generated by the energy receiver 106. For example, the signal validity-based device control module 110 may receive instructions, through the communication module from the remote system, indicating an instruction to deactivate the energy transmitter 104, the energy receiver 106, or any other components of the photoplethysmography device 100 if it is determined that signals generated by the energy receiver 106 are invalid. In various embodiments, the signal validity-based device control module 110 may control operation of the photoplethysmography device 100 based on received instructions made in response to a determination of whether the photoplethysmography device 100 is correctly positioned.

It will be understood that for some embodiments, the systems and modules or the arrangement of systems and modules may differ from what is depicted in FIG. 1.

Each of the systems, modules, analyzers, and various other components of the photoplethysmography device 100 may be implemented using one or more digital devices. An example digital device is described regarding FIG. 5. It will be appreciated that one or more of the modules may be hardware, software, or a combination of both. In some embodiments, one or more of the modules may be code within memory (e.g., a nontransitive memory such as a hard drive, SSD, flash drive, or the like). In various embodiments, one or more of the modules may include a digital signal processor (DSP) or application specific integrated chips (ASICs).

Figure 2:
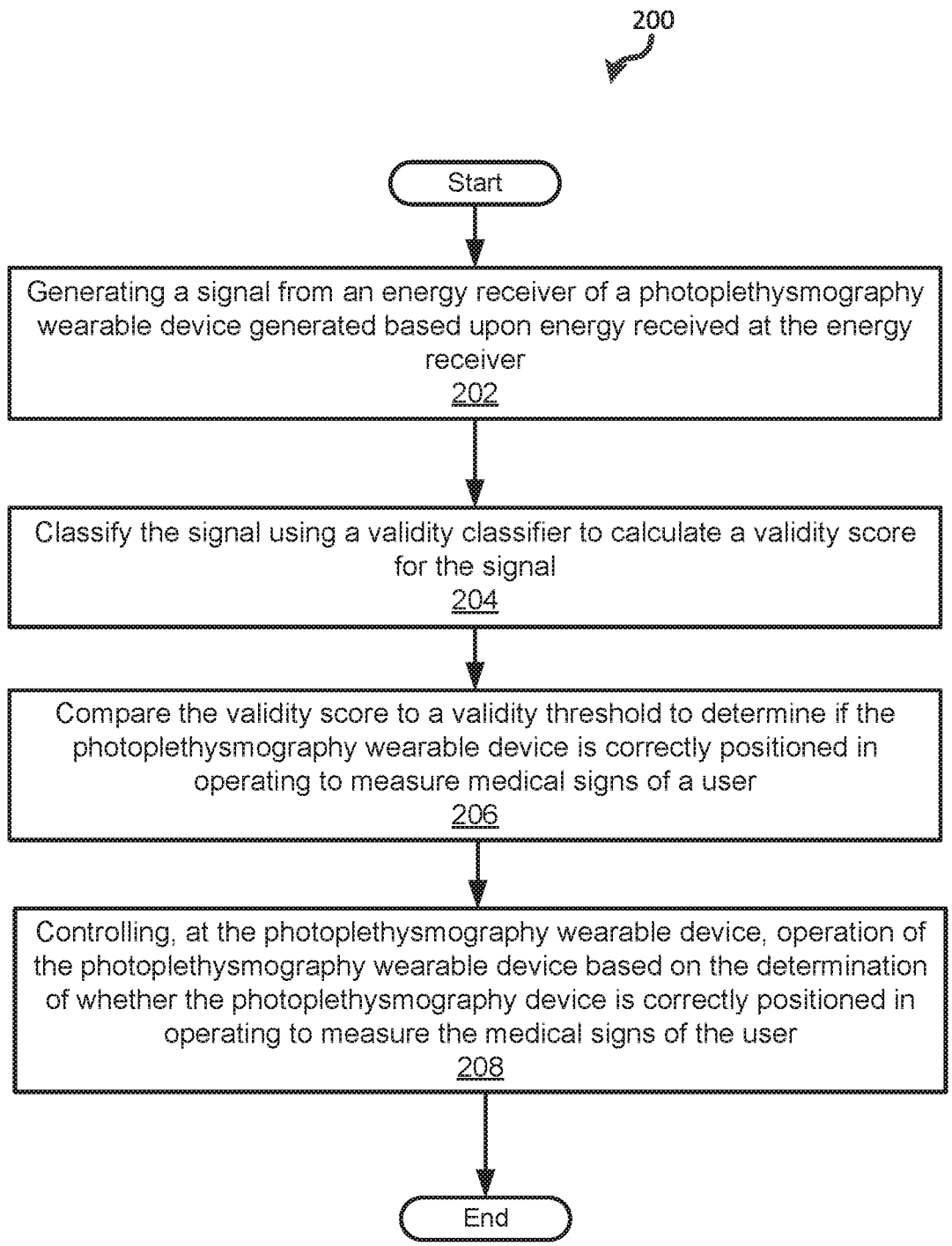
FIG. 2 illustrates an example flow diagram of a method of controlling a photoplethysmography device based on a determination of whether the photoplethysmography device is correctly positioned in operating to measure medical signs of a user.

FIG. 2 illustrates an example flow diagram of a method 200 of controlling a photoplethysmography device 100 based on a determination of whether the photoplethysmography device 100 is correctly positioned to measure medical signs of a user. At step 202, a signal is generated by the energy receiver 106 of the photoplethysmography device 100. The received signal may be generated based on energy received at the energy receiver 106. Energy received by the photoplethysmography device 100 may be initially generated by energy transmitter(s) 104 of the photoplethysmography device 100. The signal generated by the photoplethysmography device 100 may be generated (e.g., by photo detectors) based on at least a portion of the energy received by the photoplethysmography device 100.

In various embodiments, the signal generated at step 202, may be generated based on a portion of energy emitted by the energy transmitter 104 through tissue of a user and received at the energy receiver 106. For example, energy may be received at the energy receiver 106 at varying levels (e.g., intensity levels) based on an amount of energy absorbed by tissue of a user, and the received signal may be generated based on the varying energy levels of the energy received at the energy receiver 106. Alternately, the signal generated at step 202, may be generated based on energy received at the energy receiver 106 when the photoplethysmography device 100 is incorrectly positioned or not being worn. In some embodiments, wave features of the signal are extracted and wave metrics taken based on the wave features.

At step 204, the signal (e.g., wave features extracted from the signals and/or wave metrics) is classified using a validity classifier to calculate a validity score for the signal. In various embodiments, the signal may be classified using a validity classifier by the signal validity classification system 108. In various embodiments, the signal validity classification system 108 may be implemented at the photoplethysmography device 100, and may be used to determine, at the photoplethysmography device 100, whether the signal received at step 202 is valid. As discussed herein, the signal validity classification system 108 may determine at the photoplethysmography device 100 whether the photoplethysmography device 100 is correctly positioned (e.g., being worn at all or being worn correctly) to measure medical signs of a user.

At step 206, the validity score for the signal is compared to a validity threshold. The validity score for the signal may be compared to a validity threshold to determine if the photoplethysmography device 100 is correctly positioned or being worn. The signal validity classification system 108 may compare the validity score of the signal to the validity threshold to determine if the user is wearing the photoplethysmography device 100, is wearing the photoplethysmography device 100 but has the device incorrectly positioned, or is wearing the photoplethysmography device 100 in a correct position.

As discussed herein, the validity threshold may be pre-set to achieve a specific number of true positive results in determining whether signal generated by the energy receiver 106 of the photoplethysmography device 100 are actually valid. Further, in various embodiments, the validity threshold may be pre-set based on one or a combination of a device type of the photoplethysmography device 100, medical signs being measured by the photoplethysmography device 100, characteristics of a user of the photoplethysmography device 100, and/or a desired rate of achieving true positive results.

At step 208, operation of the photoplethysmography device 100 is controlled based on the determination of whether the photoplethysmography device 100 is correctly positioned (e.g., based on a comparison of the validity score to the validity threshold). For example, the signal validity-based device control module 110 controls operation of the photoplethysmography device 100 based on the determination of whether the photoplethysmography device 100 is correctly positioned.

In various embodiments, the photoplethysmography device 100 may control itself in operation (e.g. independently from a remote system) based on the determination of whether the photoplethysmography device 100 is correctly positioned. For example, the photoplethysmography device 100 may cause itself to shutoff, deactivate, or power down (e.g., sleep or hibernate) in response to a determination that the photoplethysmography device 100 is not correctly positioned.

Alternately, the photoplethysmography device 100 may be controlled by a remote system based on the determination of whether the photoplethysmography device 100 is correctly positioned. For example, the photoplethysmography device 100 may receive instructions regarding powering itself down from a remote system in response to a determination that it is incorrectly positioned. In this example, the photoplethysmography device 100 may subsequently power itself down according to the instructions.

In various embodiments, any of the energy transmitter 104, the energy receiver 106, the signal validity classification system 108, the communication module, the driver, the power source, and the analyzer may be controlled based on the determination of whether the photoplethysmography device 100 is correctly positioned. For example, the energy transmitter 104 and the energy receiver 106 may be powered off (or power reduced) in response to a determination that the photoplethysmography device 100 is incorrectly positioned.

Figure 3:
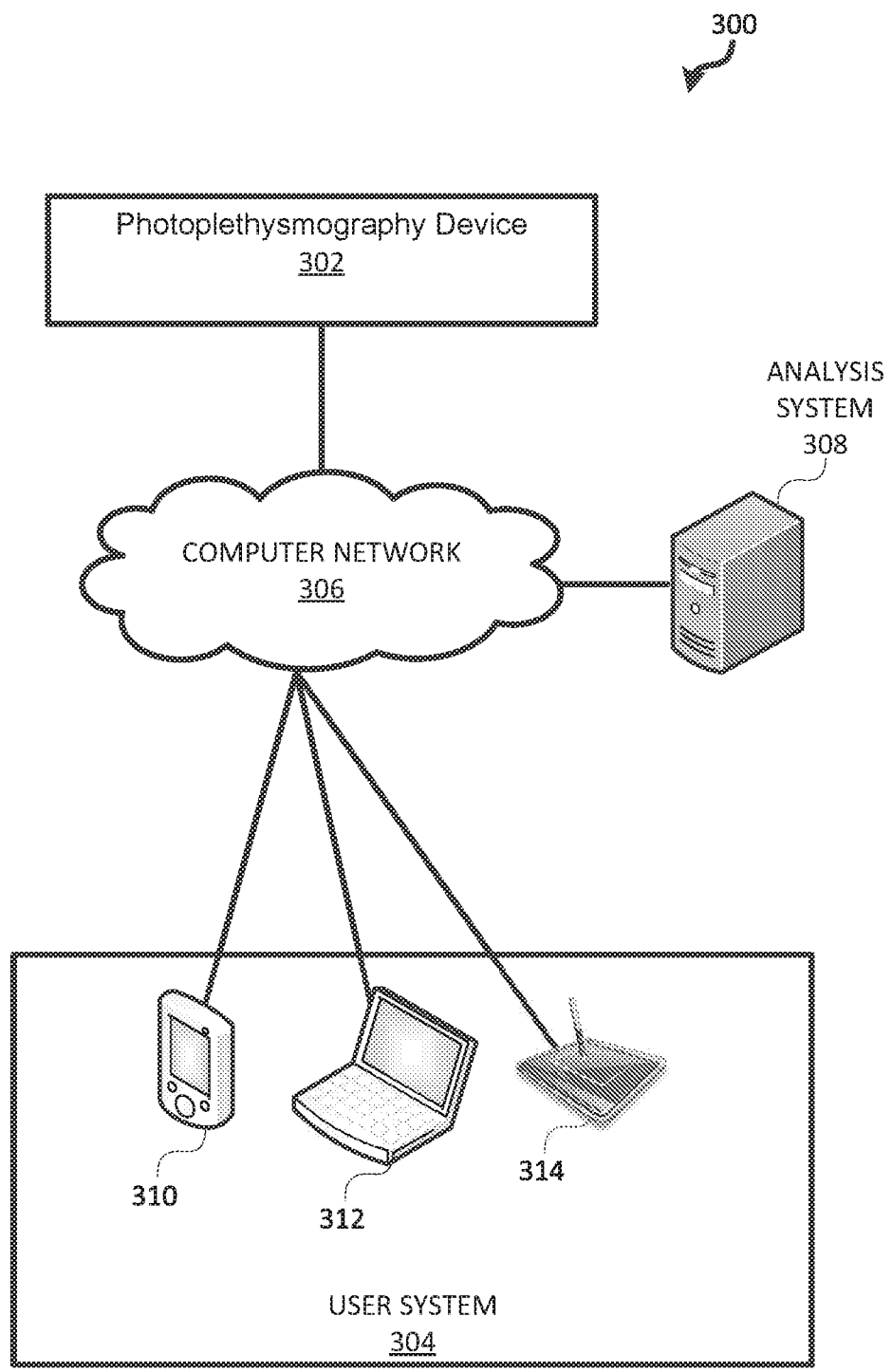
FIG. 3 is a system diagram illustrating an example environment utilizing a photoplethysmography device 302 in accordance with various embodiments.

FIG. 3 is a system diagram illustrating an example environment 300 utilizing a photoplethysmography device 302 in accordance with various embodiments. As shown in FIG. 3, the example environment 300 comprises a wearable photoplethysmography device 302, one or more user systems 304, an optional analysis system 308, and a computer network 306 communicatively coupling together each of the multispectral photoplethysmography device 302, one or more user devices 310, 312, and 314 (depicted as user system 304), and/or the analysis system 308. As shown, a user system 304 may include a smartphone 310 (e.g., iPhone®), a computer 312 (e.g., a personal computer), and/or a tablet 314 (e.g., iPad®), through the computer network 306 (e.g., a Bluetooth® 4.0 personal area network), may either interact directly or indirectly with the photoplethysmography device 302. The wearable photoplethysmography device 302 may be or include the wearable photoplethysmography device 100.

The photoplethysmography device 302 may measure medical signs non-invasively. For example, the photoplethysmography device 302 may be a multispectral blood metrics measurement apparatus configured to measure blood metrics such as concentrations of various nutrients over time, deliver energy into tissues of various body parts of a user, track a user's behavior pattern, detect motion, communicate various blood metric measurements, and/or receive a user's instructions. In various embodiments, through the computer network 306, the photoplethysmography device 302 may transmit one or more medical sign estimates or signals representing medical sign metrics to, or receive instructions from, the user system 304 or the analysis system 308, such as which medical sign metrics to measure.

In some embodiments, the photoplethysmography device 302 may project energy into tissues of a user and may receive energy through the tissues of the user. The photoplethysmography device 302 may project energy into a tissue of a user when the user is correctly wearing the photoplethysmography device 302 or, potentially, incorrectly wearing the photoplethysmography device 302. Additionally, the photoplethysmography device 302 may project energy regardless of whether the user is wearing the photoplethysmography device 302 at all.

In some embodiments, the photoplethysmography device 302 may project energy into tissue of a user and detect energy reflected from and/or transmitted through tissue of the user (e.g., the wearer of photoplethysmography device 302). The projected energy may be at multiple wavelengths that are associated with medical sign estimates (e.g. blood metrics of interest to a user). The detected energy may be a fraction of the energy that is projected into the tissue. As discussed herein, energy at different wavelengths may be absorbed at different rates, each of which may be related to a user's body state. For example, the user's body state (e.g., heart rate, blood pressure, nutrient level, or the like) may determine the amount of absorbed energy. Accordingly, energy at different wavelengths may be absorbed at different levels by a user's body. The fraction of energy received (e.g., that is reflected by the tissue or transmitted through the tissue) may be used to generate signals (e.g., composite signals) at different levels. These signals may provide information of the user's body state related to medical signs. This information may be obtained by analyzing waveforms of the signal in the time domain and/or the frequency domain.

The photoplethysmography device 302 may measure any number of medical sign metrics, including, but not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, naturally-produced chemical compound level (e.g., lactic acid), respiration rates, fluid volume, and depth of anesthesia. Nutrients may be determined based on the blood metrics to be measured. Measured nutrients may include, but are not limited to, glucose, hemoglobin, triglycerides, cholesterol, bilirubin, protein, albumin (i.e., egg white), and/or electrolytes (e.g., sodium, potassium, chloride, bicarbonate, or the like).

It will be appreciated that the user's body state may change dynamically and energy at a wavelength may be absorbed differently by a user over the time. By monitoring and tracking detected energy from the user's body, a user's health or condition may be tracked. Systems and methods described herein may monitor and store blood metrics including concentrations of various nutrients. A user's history health records may be generated, logged, and/or stored by medical signs measured at different times the wearable photoplethysmography device 302. In some embodiments, blood metrics measured by the photoplethysmography device 302 at a given time point may be compared to the history health records to detect any abnormal health conditions. The photoplethysmography device 302 may comprise a user interface where a user may input blood metrics of interest, be presented with various health reports, and/or be alerted with abnormal health conditions.

In some embodiments, a user may comfortably wear a photoplethysmography device 302 over time. The photoplethysmography device 302 may comprise lightweight components, made of hypoallergenic materials, and/or include flexible components so that it could fit various body parts (e.g., wrist, earlobe, ankle, or chest) of a user.

In accordance with some embodiments, the computer network 306 may be implemented or facilitated using one or more local or wide-area communications networks, such as the Internet, WiFi networks, WiMax networks, private networks, public networks, personal area networks ("PAN"), and the like. In some embodiments, the computer network 106 may be a wired network, such as a twisted pair wire system, a coaxial cable system, a fiber optic cable system, an Ethernet cable system, a wired PAN constructed with USB and/or FireWire connections, or other similar communication network. The computer network 306 may be a wireless network, such as a wireless personal area network, a wireless local area network, a cellular network, or other similar communication network. Depending on the embodiment, some or all of the communication connections associated with the computer network 306 may utilize encryption (e.g., Secure Sockets Layer [SSL]) to secure information being transferred between the various entities shown in the example environment 300.

Although FIG. 3 depicts a computer network 306 supporting communication between different digital devices, it will be appreciated that the photoplethysmography device 302 may be directly coupled (e.g., over a cable) with any combination of the user devices 310, 312, and 314.

The user devices 310-314 may include any digital device capable of executing an application that measures, assists in measuring, or posting results related to blood metrics. An application user interface may be presented by the application and/or communicating with various entities in the example environment 300 through the computer network 306. For instance, the user device 310 may receive one or more medical sign measurements from the photoplethysmography device 302 (e.g., via the computer network 306), track and store the medical sign measurements, analyze the medical sign measurements, and/or provide recommendations based on the medical sign measurements. An application user interface may facilitate interaction between a user of the user system 304 and an application running on the user system 304.

In various embodiments, any of the user devices 310-314 may perform analysis of the medical sign measurements using data received from the photoplethysmography device 302, display results, provide reports, display progress, display historic readings, track measurements, track analysis, provide alerts, and/or the like.

The analysis system 308 may be or include any digital device capable of executing an analysis application for analyzing and/or measuring medical sign metrics. In some embodiments, the analysis system 308 may generate reports or generate alerts based on analysis or measurement of medical sign metrics. For instance, through the computer network 306, the analysis system 308 may receive one or more blood metric measurements from the photoplethysmography device 302, track and store blood metric measurements, analyze blood metric measurements, and/or provide recommendations based on the analysis. An application programming interface may facilitate interaction between a user, the user devices 310-314, and/or the multispectral blood metrics measurement apparatus 310 with the analysis system 308.

In some embodiments, the photoplethysmography device 302, user devices 310-314, and/or analysis system 308 may comprise a reference table for measuring medical sign metrics. For example, the photoplethysmography device 302, user devices 310-314, and/or analysis system 308 may comprise a reference table of blood components, molecules, and/or nutrients and wavelengths corresponding to the blood components, molecules, and/or nutrients. A wavelength may be unique to or more generally associated with a nutrient. A reference wavelength may be unique to or more generally associated with a combination of nutrients to be measured. As such, wavelength(s) may be determined by looking up each blood components, molecules, and/or nutrients that is to be measured. Energy at the determined wavelengths may be transmitted by an energy transmitter of the photoplethysmography device 302 into the body.

Computing devices (e.g., digital devices) may include a mobile phone, a tablet computing device, a laptop, a desktop computer, personal digital assistant, a portable gaming unit, a wired gaming unit, a thin client, a set-top box, a portable multi-media player, or any other type of network accessible user device known to those of skill in the art. Further, the analysis system 308 may comprise of one or more servers, which may be operating on or implemented using one or more cloud-based services (e.g., System-as-a-Service [SaaS], Platform-as-a-Service [PaaS], or Infrastructure-as-a-Service [IaaS]).

It will be understood that for some embodiments, the components or the arrangement of components may differ from what is depicted in FIG. 3.

Each of the photoplethysmography device 302, one or more user devices 310, 312, and 314, and the analysis system 308 may be implemented using one or more digital devices. An example digital device is described regarding FIG. 5.

Figure 4:
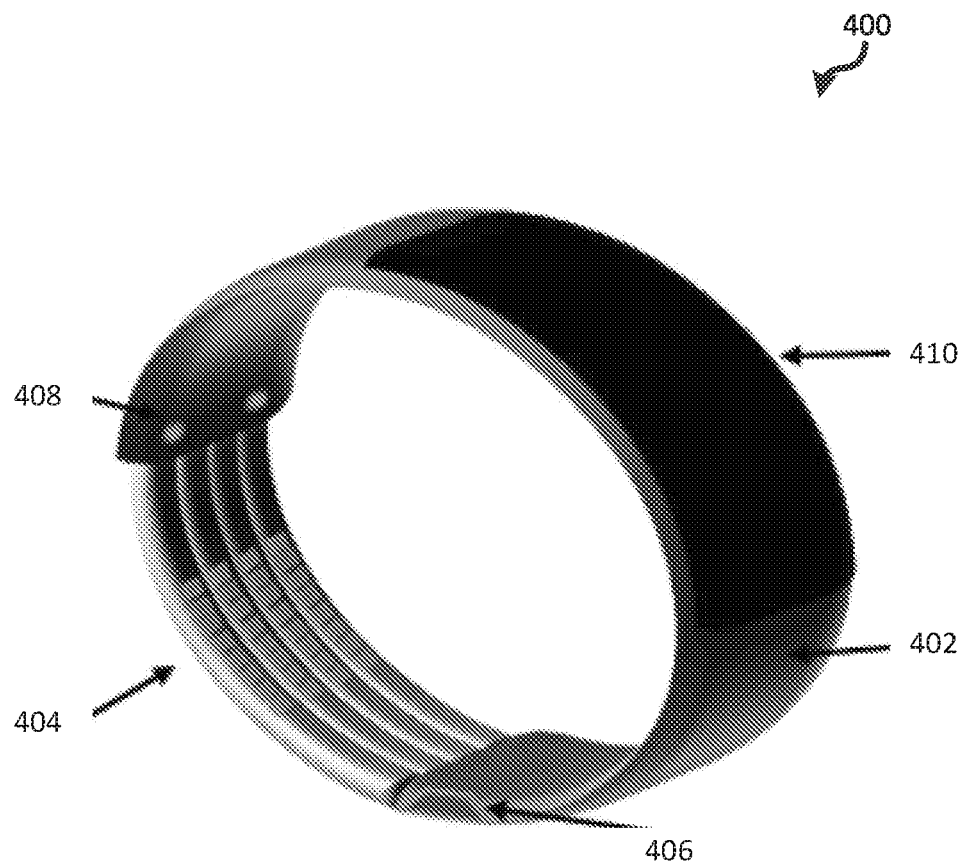
FIG. 4 illustrates an example photoplethysmography device for measuring various medical signs in accordance with embodiments of the present application.

FIG. 4 illustrates an example photoplethysmography device 400 for measuring various medical signs in accordance with embodiments of the present application. The photoplethysmography device 400 comprises a central unit 402, a sensor array 404, and a coupling means 408. The central unit 402 may be a wearable member made of elastic and/or flexible hypoallergenic wearable material. The photoplethysmography device 400 may be or include the photoplethysmography device 302.

In the illustrated example, the sensor array 404 is coupled to the central unit 402. The sensor array 404 may comprise any number of energy transmitters and/or energy receivers. In some embodiments, the sensor array 404 may be detached from the central unit 402. The sensor array 404 may be mechanically and/or electrically coupled to the central unit 402. The sensor array 404 comprises various illumination (e.g., near infra-red, infra-red, or short infra-red) and sensing arrays. An illumination array may include any number of energy transmitters (e.g., any number of energy transmitter 104). A sensing array may include any number of energy receivers (e.g., any number of energy receivers 106). The sensor array 404 may further comprise conductivity and/or capacity sensors. Different sensor array 404 may be provided to measure different medical signs.

The central unit 402 may comprise an analyzer, one or more energy transmitter(s), and/or one or more energy receiver(s). The central unit 402 may further comprise a communication module and/or a battery compartment. The coupling means 408 may be mounting screw holes in FIG. 4, however, it will be appreciated that coupling means may be optional. The coupling means 408 may include or be any kind of coupling means including a clip, hook, switch, expanding fabric, adhesive, or the like. It will be appreciated that other mounting means may be used.

The photoplethysmography device 400 further comprises a micro-USB port 406 to allow for communication with a digital device and a screen 410. Various user interfaces (e.g., lights, a display, touchscreen, or the like) may be displayed on the screen 410.

Figure 5:
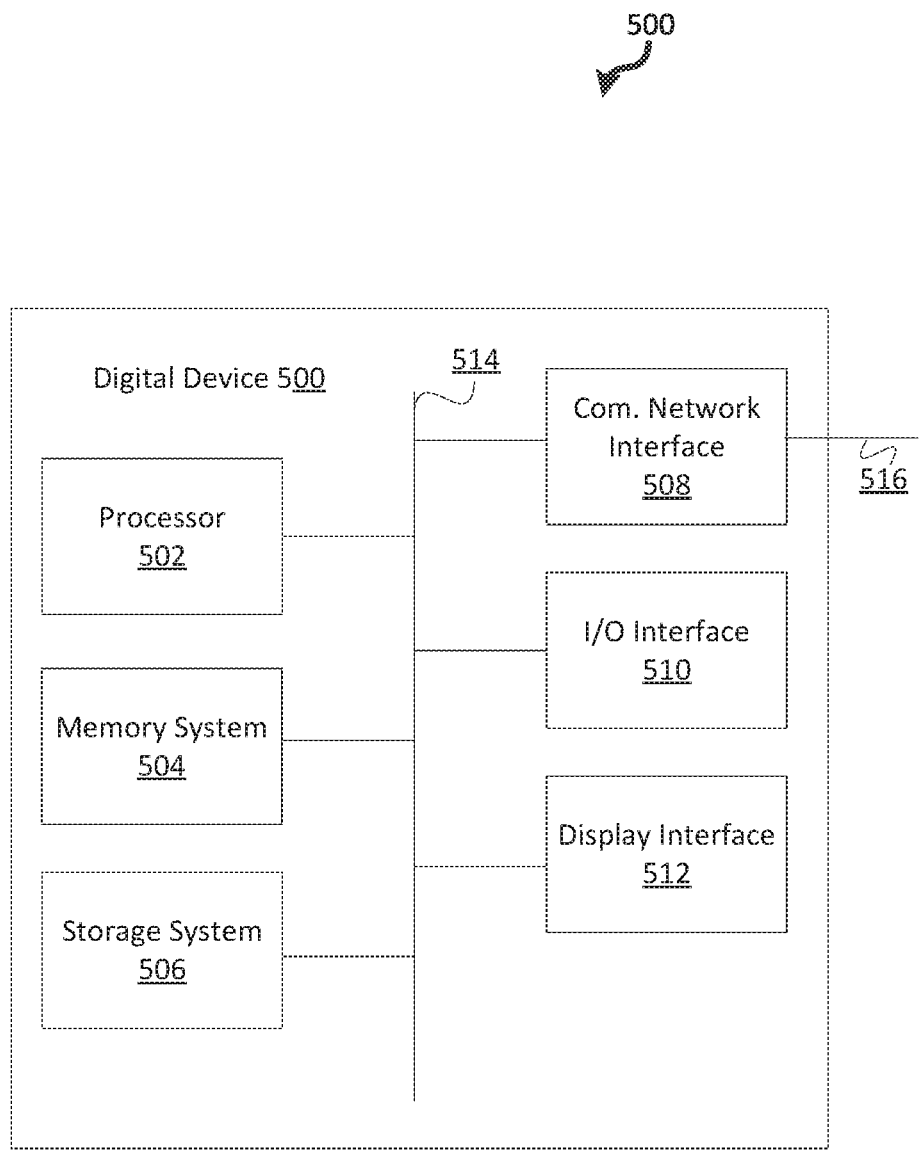
FIG. 5 is a block diagram of an example digital device.

FIG. 5 is a block diagram of an example digital device 500. The digital device 500 comprises a processor 502, a memory system 504, a storage system 506, a communication network interface 508, an I/O interface 510, and a display interface 512 communicatively coupled to a bus 514. The processor 502 is configured to execute executable instructions (e.g., programs). In some embodiments, the processor 502 comprises circuitry or any processor capable of processing the executable instructions.

The memory system 504 is any memory configured to store data. Some examples of the memory system 504 are storage devices, such as RAM or ROM. The memory system 504 may comprise the RAM cache. In various embodiments, data is stored within the memory system 504. The data within the memory system 504 may be cleared or ultimately transferred to the storage system 506.

The storage system 506 is any storage configured to retrieve and store data. Some examples of the storage system 506 are flash drives, hard drives, optical drives, and/or magnetic tape. In some embodiments, the digital device 500 includes a memory system 504 in the form of RAM and a storage system 506 in the form of flash data. Both the memory system 504 and the storage system 506 comprise computer readable media which may store instructions or programs that are executable by a computer processor including the processor 502.

The communications network interface (com. network interface) 508 may be coupled to a network (e.g., the computer network 304) via the link 516. The communication network interface 508 may support communication over an Ethernet connection, a serial connection, a parallel connection, or an ATA connection, for example. The communication network interface 508 may also support wireless communication (e.g., 802.11 a/b/g/n, WiMax). It will be apparent to those skilled in the art that the communication network interface 408 may support many wired and wireless standards.

The optional input/output (I/O) interface 510 is any device that receives input from the user and output data. The optional display interface 512 is any device that is configured to output graphics and data to a display. In one example, the display interface 512 is a graphics adapter.

It will be appreciated that the hardware elements of the digital device 500 are not limited to those depicted in FIG. 5. A digital device 500 may comprise more or less hardware elements than those depicted. Further, hardware elements may share functionality and still be within various embodiments described herein. In one example, encoding and/or decoding may be performed by the processor 502 and/or a co-processor located on a GPU (i.e., Nvidia®).

Figure 6:
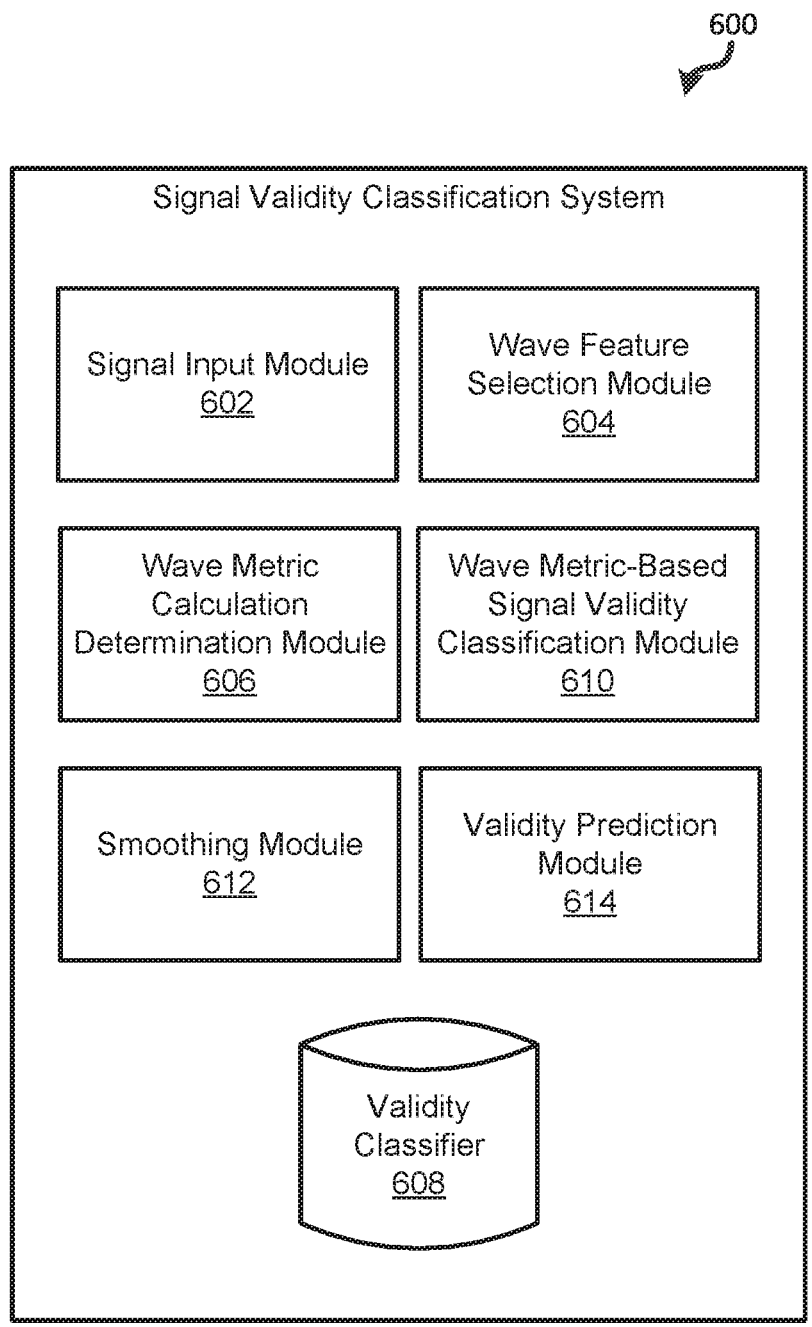
FIG. 6 is a block diagram of an example signal validity classification system.

FIG. 6 is a block diagram of an example signal validity classification system 600. The signal validity classification system 600 determines validity of a signals and/or energy received by an energy receiver 106 at the photoplethysmography device 100 (see FIG. 1). The signal validity classification system 600 may determine validity of a received signal based on a portion of energy transmitted from the energy transmitter to the energy receiver of the photoplethysmography device 100 when the photoplethysmography device 100 is operating to measure medical signs while not being worn or otherwise is incorrectly positioned.

In various embodiments, the signal validity classification system 600 may determine validity of the signals and/or energy based on optical beam(s) or other energy transmitted from an energy transmitter at a photoplethysmography device 100. For example, the signal validity classification system 600 may determine validity of a received signal based on a portion of energy directed to tissue of a user by the energy transmitter of a photoplethysmography device 100 after passing through, reflecting off of, or otherwise interacting with at least some tissue of a user.

The signal validity classification system 600 may determine validity of a received signal when the photoplethysmography device 100 is not worn. For example, the signal validity classification system 600 may determine validity of a received signal based on a portion of energy transmitted from the energy transmitter to the energy receiver of the photoplethysmography device 100 without that energy passing through, reflecting off of, or otherwise interacting with at least some tissue of a user.

In various embodiments, the signal validity classification system 600 may determine whether the photoplethysmography device 100 is correctly positioned to measure medical signs of a user. For example, the signal validity classification system 600 may determine the photoplethysmography device 100 is not being worn at all. In another example, as part of determining that the photoplethysmography device 100 is incorrectly positioned, the signal validity classification system 600 may determine the photoplethysmography device 100 is being worn but has incorrect placement to enable functionality.

In various embodiments, the signal validity classification system 600 is implemented at a photoplethysmography device 100. The signal validity classification system 600 may determine whether signals generated at the photoplethysmography device 100 are valid.

Alternately, all or portions of the signal validity classification system 600 may be implemented remote from the photoplethysmography device 100. In being implemented remotely from the photoplethysmography device 100, the signal validity classification system 600 may remotely determine whether signals generated at the photoplethysmography device 100 are valid. For example, the signal validity classification system 600 may, at a remote location, receive a signal generated at the photoplethysmography device 100 (e.g., by the energy receiver in response to detecting energy initially transmitted by the energy transmitter), determine whether the signal(s)/energy received by the photoplethysmography device 100 are valid, and potentially allow for remote control of operation (e.g., instructions to activate parts of the photoplethysmography device 100, deactivate parts of the photoplethysmography device 100, continue to perform additional tests and analysis to estimate medical conditions/signs of the user, perform a subset of tests and analysis to estimate medical conditions/signs of the user, test validity of received signal(s) again, and/or the like).

In various embodiments, a determination of whether signals received at a photoplethysmography device 100 are valid, as made by the signal validity classification system 600, may be used to control operation of the photoplethysmography device. For example, one or a combination of an energy transmitter 104, an energy receiver 106, a signal validity classification system 108, a communication module, a driver, a power source, an analyzer, and other applicable modules or components of a photoplethysmography device may be controlled based on a determination of whether signals generated at the photoplethysmography device are valid.

The signal validity-based device control module 110 may control operation of the photoplethysmography device 100 based on a determination of whether signals received at the photoplethysmography device 100 are valid. For example, the signal validity-based device control module 110 may control operation of one or a combination of an energy transmitter 104, an energy receiver 106, a signal validity classification module 110, a communication module, a driver, a power source, an analyzer, and other applicable modules or components of a photoplethysmography device 100 may be controlled based on a determination, as made by the signal validity classification system 600, of whether signals generated at the photoplethysmography device 100 are valid.

The example signal validity classification system 600 shown in FIG. 6 includes a signal input module 602, a wave feature selection module 604, a wave metric calculation determination module 606, a validity classifier datastore 608, a wave metric-based signal validity classification module 610, a smoothing module 612, and a validity prediction module 614. The signal input module 602 may receive signals generated at a photoplethysmography device 100 based on energy received by an energy receiver 106 of the photoplethysmography device 100 (e.g., signals generated by a photo detector that detected light energy reflected from the tissue of the user).

In various embodiments, the signal input module 602 receives signals generated at a photoplethysmography device 100 based on at least a portion of energy emitted from an energy transmitter 104 of the photoplethysmography device 100 and received at an energy receiver 106 of the photoplethysmography device 100. For example, the signal input module 602 may receive a signal generated based on a portion of energy initially generated by the energy transmitter 104 of the photoplethysmography device 100 and received at the energy receiver 106 after passing through, reflecting off of, or otherwise interacting with the tissue. In another example, the signal input module 602 may receive a signal generated based on a portion of energy transmitted from the energy transmitter 104 to the energy receiver 106 of the photoplethysmography device 100 without passing through, reflecting off of, or otherwise interacting with tissue of the user.

The wave feature selection module 604 selects (or "extracts") a subset of wave features from a plurality of wave features of the signal received from the signal input module 602. As discussed herein, the signal(s) as well as wave features of the signal(s) generated by the energy receiver 106 are related to the detected energy. Wave features include applicable features associated with a wave of a signal. For example, wave features may include waves, wave peaks, wave valleys, wave edges, and/or the like.

The wave feature selection module 604 may select waves from the signal received by the signal input module 602 for use in selecting wave features from the signal. The wave feature selection module 604 may select "high quality" waves from the signal that match typical waves generated by the photoplethysmography device 100 for measuring a specific medical sign. For example, the wave feature selection module 604 may select waves with generally desired wave features. In some embodiments, the wave feature selection module 604 may select waves to extract wave features based on one or a combination of medical signs the photoplethysmography device 100 may measure, characteristics of a user of the photoplethysmography device 100, and/or a device type of the photoplethysmography device 100.

The wave feature selection module 604 may select waves from the signal according to wave selection rules. For example, the wave feature selection module 604 may identify the wave valleys whose frequency matches with the heart rate of the user and then checking how close the wave is to a bi-Gaussian model, according to wave selection rules, as part of selecting waves according to wave selection rules. The wave selection rules may be provided remotely, by the user (e.g., through an application that communicates with the photoplethysmography device 100 or an interface on the photoplethysmography device 100), or previously configured within the photoplethysmography device 100.

In various embodiments, the wave feature selection module 604 may normalize the signal(s) received by the signal input module 602, as part of selecting a subset of wave features from the plurality of wave features of the signal. For example, the wave feature selection module 604 may divide the signal by the mean of the signal and subtract the new signal mean of one from the signal to normalize the signal. It will be appreciated that any normalization may be used.

The wave metric calculation determination module 606 determines wave metric calculations based on the selected wave features. In various embodiments, the wave metric calculation determination module 606 determines wave metric calculations of a set of the potential wave metric calculations described with reference to FIG. 1. For example, a set of wave metric calculations may include one or a combination of signal energy measurements, signal mobility measurements, signal complexity measurements, signal crossing rate measurements, and signal non-oscillatory component measurements.

In various embodiments, the wave metric calculation determination module 606 may determine wave metric calculations for the signal received by the signal input module 602 based on the wave features selected by the wave feature selection module 604 from the signal. For example, the wave metric calculation determination module 606 may determine one or a combination of signal energy measurements, signal mobility measurements, signal complexity measurements, signal crossing rate measurements, and signal non-oscillatory component measurements based on the wave features selected by the wave feature selection module 604. The wave metric calculation determination module 606 may determine wave metric calculations for the signal by independently determining corresponding wave metric calculations for each of the subset of wave features of the plurality of wave features selected by the wave feature selection module 604. For example, the wave metric calculation determination module 606 may separately determine signal mobility measurements and signal complexity measurements for the each of the selected subset of wave features of the plurality of wave features of the signal, as part of determining wave metric calculations for the signal.

The validity classifier datastore 608 may store one validity classifier or a plurality of data classifiers. In some embodiments, the validity classifier datastore 608 stores validity classifier data indicating any number of validity classifiers of a plurality of validity classifiers capable of being applied to wave metric calculations, for use in determining validity of the signal received by the signal input module 602. In various embodiments, the validity classifier datastore 608 may store validity classifier data indicating a validity classifier based on wave metric calculations, potentially including the set of wave metric calculations determined by the wave metric calculation determination module 606. The validity classifier datastore 608 may store a validity classifier including a range of values of signal mobility measurements for application to signal mobility measurements of the signal, as determined by the wave metric calculation determination module 606.

In various embodiments, the validity classifier datastore 608 stores a validity classifier associated with or specific to any number of characteristics of a user of a photoplethysmography device 100. For example a validity classifier stored in the validity classifier datastore 608 may be specific to males within a certain age range exhibiting similar medical signs.

In various embodiments, the validity classifier datastore 608 stores validity thresholds for use in comparing to validity scores determined through application of a validity classifier to wave metric calculations. For example, the validity classifier datastore 608 may store a validity threshold specifying a specific validity score or range of validity scores to compare determined validity scores. The comparison may assist in determining whether a user of the photoplethysmography device 100 is correctly wearing the device. A validity threshold stored in the validity classifier datastore 608 may be specific to a validity classifier. For example, a validity threshold specific to a validity classifier may be applied when validity scores are determined for a signal using the validity classifier.

In various embodiments, the validity classifier datastore 608 stores one or a plurality of pre-set and selectable validity thresholds. A pre-set and selectable validity threshold stored in the validity classifier datastore 608 may be specific to one or a combination of a device type of a photoplethysmography device 100, medical signs being estimated by the photoplethysmography device 100, characteristics of a user of the photoplethysmography device 100, and a desired rate of achieving true positive results. For example, a validity classifier stored in the validity classifier datastore 608 may include a validity threshold specific to achieving a certain number of true positive results, in applying a validity classifier in determining validity of signals received by a photoplethysmography device measuring blood pressure or medical signs in females over the age of fifty.

The pre-set and selectable validity thresholds stored in the validity classifier datastore 608 may be specifically associated with a validity classifier. For example, the validity classifier datastore 608 may store pre-set and selectable validity thresholds to use with a specific classifier in determining validity of signals generated for measuring different medical signs using the specific classifier.

The wave metric-based signal validity classification module 610 classifies the signal using a validity classifier. In various embodiments, the wave metric-based signal validity classification module 610 may apply the validity classifier, as indicated by validity classifier data stored in the validity classifier datastore 608, to the wave metric calculations of the set of wave metric calculations to generate one or a plurality of validity scores. For example, the wave metric-based signal validity classification module 610 may input the wave metric calculations into a function, included as part of the validity classifier, to determine if the results fall within a range of values of the function, as part of applying the validity classifier. Further in the example, the validity classification module 610 may input the wave metric calculations into a trained support vector machine forming part of the classifier. In classifying the signal using the validity classifier, the wave metric-based signal validity classification module 610 may generate one or a plurality of validity scores for the signal, for use in determining whether the received signals are valid (i.e., may be used to estimate medical signs of the user). For example, in classifying the signal using the validity classifier, the wave-metric based signal validity classification module 610 may apply a validity classifier to corresponding wave metric calculations generated for each (or one or more) wave feature of the set of wave features, to generate a plurality of validity scores corresponding to the respective each wave feature of the set of wave features.

In various embodiments, the wave metric-based signal validity classification module 610 applies a classifier fit to a logistic function to the wave metric calculations. For example, the wave metric-based signal validity classification module 610 may apply a classifier fit to the logistic function as shown in Example Equation 7 herein. In applying a classifier fit to a logistic function to the wave metric calculations, the wave metric-based signal validity classification module 610 may calculate a validity score falling within a specific range of values based on a logistic function. For example, the wave metric-based signal validity classification module 610 may apply a validity classifier fit to a logistic function to the wave metric calculations to generate a validity score falling between 0 and 1.

In various embodiments, the wave metric-based signal validity classification module 610 selects a specific validity classifier to apply to the wave metric calculations. The wave metric-based signal validity classification module 610 may select a specific classifier to apply to the wave metric calculations based on one or a combination of a device type of a photoplethysmography device 100, medical signs being measured by the photoplethysmography device 100, characteristics of a user of the photoplethysmography device 100, and a desired rate of achieving true positive results. For example, the wave metric-based signal validity classification module may apply a validity classifier specific to a photoplethysmography device 100 used in determining respiration rates of patients.

The smoothing module 612 optionally applies temporal smoothing to the resulting validity scores generated through application of the validity classifier to the wave metric calculations to generate a smoothed validity score. The smoothing module 612 may apply an applicable temporal smoothing method, e.g. a rank smoothing method, to the resulting validity scores generated through application of the validity classifier to the wave metric calculations. For example, the smoothing module 612 may apply a rank filter causing selection of the third highest validity score of the previous eight determined validity scores as a smoothed validity score. In various embodiments, as the wave metric-based signal validity classification module 610 may determine each validity score independently, application of smoothing may reduce noise causing prediction errors.

The validity prediction module 614 compares one or a plurality of the determined validity scores to a validity threshold to determine if the photoplethysmography device 100 is correctly positioned to measure (e.g., estimate) medical signs of a user. In various embodiments, the validity prediction module 614 may determine the photoplethysmography device 100 is correctly positioned if one or a combination of the plurality of the determined validity scores are above a validity threshold. For example, if a majority of the validity scores generated for the signal fall above a validity threshold, then the validity prediction module 614 may determine the photoplethysmography device 100 is positioned correctly. In various embodiments, the validity prediction module 614 may compare a determined smoothed validity score, as filtered using the smoothing module 612, to a validity threshold to determine if the photoplethysmography device 100 is correctly positioned to measure medical signs of a user. For example, if a determined smoothed validity score filtered using the smoothing module 612 is above a validity threshold, then the validity prediction module 614 may determine the photoplethysmography device 100 is correctly positioned.

In various embodiments, the validity prediction module 614 may select a pre-set validity threshold to compare to one or a plurality of validity thresholds for determining validity of the received signal. The validity prediction module 614 may select a pre-set validity threshold based on a validity classifier chosen by the wave-metric based signal validity classification module 610. Additionally, the validity prediction module 614 may select a pre-set validity threshold based on one or a combination of a device type of a photoplethysmography device 100, medical signs being measured by the photoplethysmography device 100, characteristics of a user of the photoplethysmography device 100, and a desired rate of achieving true positive results. For example, if the photoplethysmography device 100 is used to measure blood pressure, then a pre-set and selectable validity threshold used in determining validity of signals generated by photoplethysmography devices 100 may be selected by the validity prediction module 614.

It will be understood that for some embodiments, the modules and datastores or the arrangement of modules and datastores may differ from what is depicted in FIG. 6.

Each of the modules and datastore of the signal validity classification system 600 may be implemented using one or more digital devices. An example digital device is described regarding FIG. 5.

Figure 7:
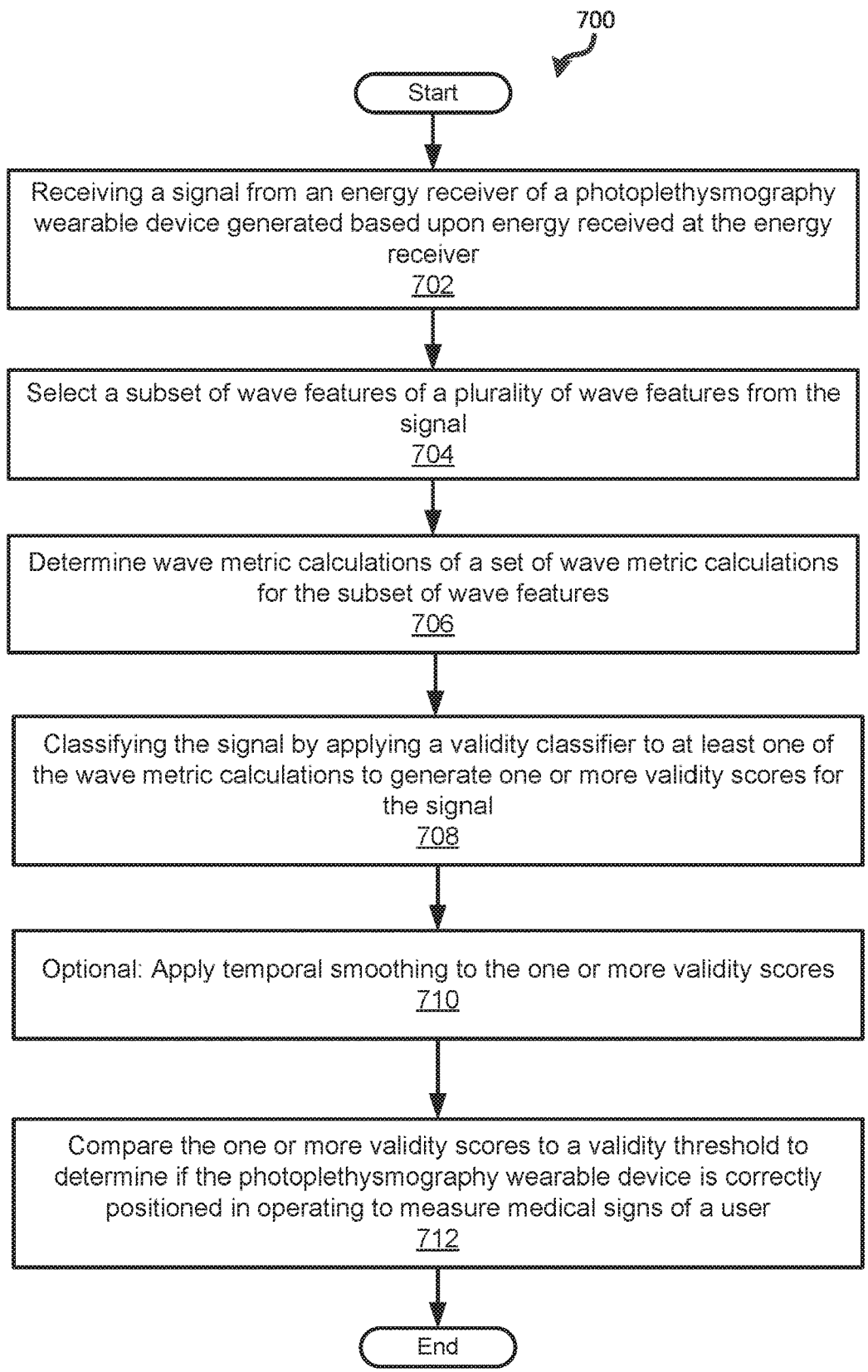
FIG. 7 depicts an example flow diagram of a method of determining whether a photoplethysmography device is positioned correctly by applying a validity classifier to a signal generated by the photoplethysmography device in operation.

FIG. 7 depicts an example flow diagram of a method 700 of determining whether a photoplethysmography device 100 is positioned correctly by applying a validity classifier to a signal generated by the photoplethysmography device 100 in operation. In various embodiments, the method 700 is implemented by the signal validity classification system 600. The validity classification system 600 performing the steps of the method 700 may be implemented at a photoplethysmography device 100, for purposes of determining at the photoplethysmography device 100 whether the device is correctly positioned to measure medical signs of a user. Additionally, the validity classification system 600 performing the steps of the method 700 may be implemented remote from a photoplethysmography device 100, for purposes of determining remotely from the photoplethysmography device 100, whether the device is correctly positioned.

At step 702, optical beam(s) and/or signal(s) are received from an energy receiver of a wearable photoplethysmography device 100. The optical beam(s) and/or signal(s) may be initially transmitted from an energy transmitted through tissue(s) of the user. The energy receiver may receive the optical beam(s) and/or signals through the tissues of the user (e.g., the energy receiver may receive that energy that was not absorbed or reflected away from the energy receiver). The energy receiver may generate one or more signals based on the optical beam(s) and/or signal(s) received or detected. The signal may be received from an energy receiver of the wearable photoplethysmography device 100 by the signal input module 602.

In various embodiments, the signal received at step 702 may be received even if the wearable photoplethysmography device 100 is not positioned correctly to measure medical signs of a user. The signal received at step 702 may be generated based on energy received at an energy receiver, when a user is not wearing a wearable photoplethysmography device. In various embodiments, the signal received at step, may be generated based on energy received at an energy receiver, when a user is wearing a wearable photoplethysmography device 100 but it is not positioned correctly to measure medical signs of a user.

At step 704, a subset of wave features of a plurality of wave features are selected from the signal generated by the energy receiver in response to detecting the optical beam(s) and/or signal(s). The wave feature selection module 604 may select the plurality of wave features from the signal. In various embodiments, specific waves of the signal to extract wave features from may be selected from the signal. Waves of the signal to extract wave features from may be selected based on one or a combination of medical signs the wearable photoplethysmography device 100 is estimating or measuring, characteristics of a user of the wearable photoplethysmography device 100, and/or a device type of the wearable photoplethysmography device 100. For example, specific waves of the signal to extract wave features from may be selected based on if the wearable photoplethysmography device 100 is being used to measure blood pressure of a user. Further, in various embodiments, specific waves to extract wave features from may be selected from the signal based on wave selection rules. For example, wave valleys whose frequency matches a heart rate of a user may be determined according to wave selection rules and subsequently waves corresponding to the wave valleys may be selected for use in extracting wave features.

In various embodiments, the signal may be normalized before wave features of a plurality of wave features of the signal are selected. For example, the signal may be divided by a mean of the signal and the new signal mean of one may be subtracted from the signal to normalize the signal.

At step 706, wave metric calculations of a set of wave metric calculations are determined from the subset of wave features of the plurality of wave features selected from the signal. The wave metric calculation determination module 606 may determine wave metric calculations of a set of wave metric calculations from the subset of wave features of the plurality of wave features selected from the signal. In various embodiments, wave metric calculations of a set of the potential wave metric calculations described with reference to FIG. 1 are determined from the subset of wave features of the plurality of wave features. For example, a set of wave metric calculations determined from the subset of wave features may include one or a combination of signal energy measurements, signal mobility measurements, signal complexity measurements, signal crossing rate measurements, and signal non-oscillatory component measurements.

In various embodiments, wave metric calculations may be determined independently for each of the subset of wave features of the plurality of wave features selected for the signal. For example, the wave metric calculation determination module 606 may determine separate signal mobility measurements and signal complexity measurements for each wave feature of the subset of wave features of the plurality of wave features of the signal, as part of determining wave metric calculations for the subset of wave features.

At step 708, the signal is classified by applying a validity classifier to at least one of the wave metric calculations to generate one or more validity scores for the signal. The wave metric-based signal validity classification module 610 may classify the signal by applying a validity classifier to at least one of the wave metric calculations to generate one or more validity scores for the signal. A validity classifier may be applied to at least one of the wave metric calculations using validity classification data stored in the validity classifier datastore 608.

In various embodiments, a specific validity classifier to apply to at least one of the wave metric calculations to generate one or more validity scores for the signal may be selected. A specific classifier to apply to the at least one of the wave metric calculations may be selected based on one or a combination of a device type of the wearable photoplethysmography device 100, medical signs being measured by the wearable photoplethysmography device 100, characteristics of a user of the wearable photoplethysmography device 100, and a desired rate of achieving true positive results. For example, the wave metric-based signal validity classification module may apply a validity classifier specific to the wearable photoplethysmography device 100 if the device is used in determining respiration rates of patients.

In various embodiments, a specific validity classifier applied to at least one of the wave metric calculations is fit to a logistic function. For example, the validity classifier may be fit to a logistic to cause the resulting one or more validity scores created through application of a specific validity classifier to fall between the values of 0 and 1.

At optional step 710, temporal smoothing is applied to one or more of the validity scores to generate a smoothed validity scores. The smoothing module 602 may apply temporal smoothing to the one or more validity scores to generate a smoothed validity score using an applicable temporal smoothing method. For example, a rank smoothing method may be applied to the one or more of the validity scores to generate a smoothed validity score.

At step 712, the one or more validity scores are compared to a validity threshold to determine if the wearable photoplethysmography device 100 is correctly positioned in operating to measure medical signs of a user. The validity prediction module 614 may compare the one or more validity scores to a validity threshold to determine if the wearable photoplethysmography device 100 is correctly positioned. For example, if a majority of validity scores fall above a validity threshold, then it may be determined that the wearable photoplethysmography device is correctly positioned. Conversely, in another example, if a majority of validity scores fall below a validity threshold, then it may be determined that the wearable photoplethysmography device 100 is incorrectly positioned in operating to measure medical signs of a user.

In various embodiments, a smoothed validity score may be compared to a validity threshold to determine if the wearable photoplethysmography device 100 is correctly positioned in operating to measure medical signs of a user. For example, if a smoothed validity score falls above a validity threshold, then it may be determined the wearable photoplethysmography device 100 is correctly positioned in operating to measure medical signs of a user.

In various embodiments, a validity threshold applied at step 712 is selected pre-set validity threshold. A validity threshold applied at step 712 may be selected based on the validity classifier applied at step 708. For example, a specific validity threshold associated with the validity classifier may be selections. Additionally, a validity threshold applied at step 712 may be selected based on one or a combination of a device type of the wearable photoplethysmography device 100, medical signs being measured by the wearable photoplethysmography device 100, characteristics of a user of the wearable photoplethysmography device 100, and a desired rate of achieving true positive results. For example, if the wearable photoplethysmography device 100 is used to measure blood pressure, then a validity threshold specific to determining whether signals generated by wearable photoplethysmography devices 100 measuring blood pressure are valid may be selected and applied at step 712.

Figure 8:
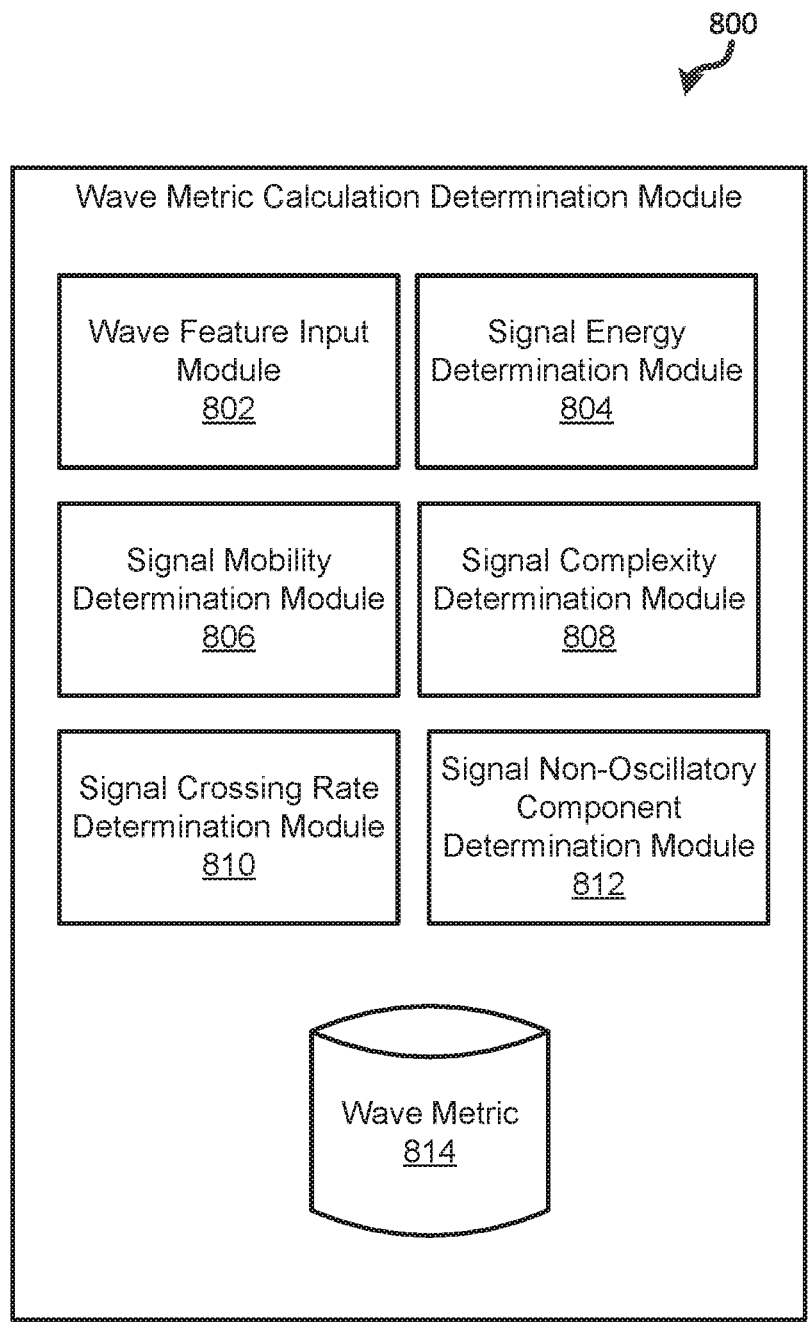
FIG. 8 is a block diagram of an example wave metric calculation determination module.

FIG. 8 is a block diagram of an example wave metric calculation determination module 800. The wave metric calculation determination module 800 determines wave metric calculations from a signal received from the energy receiver to determine if a photoplethysmography device 100 that generated the signal is correctly positioned in operating to measure medical signs of a user. The wave metric calculation determination module 800 may determine wave metric calculations for a subset of wave features of a plurality of wave features selected from a signal generated by a photoplethysmography device. Additionally, the wave metric calculation determination module 800 may independently determine wave metric calculations for each wave feature of a subset of wave features selected from a signal.

The example signal validity classification system 800 shown in FIG. 8 includes a wave feature input module 802, a signal energy determination module 804, a signal mobility determination module 806, a signal complexity determination module 808, a signal crossing rate determination module 810, a signal non-oscillatory component determination module 812, and a wave metric datastore 814. The wave feature input module 802 receives wave features selected from a signal generated by a photoplethysmography device 100. The wave feature input module 802 may receive wave features selected by the wave feature selection module 604. For example, the wave feature input module 802 may receive a subset of wave features selected from a plurality of wave features of a signal.

In various embodiments, the wave feature input module 802 receives wave features selected from a normalized signal. The wave feature input module 802 may receive wave features selected from a signal normalized according to an applicable signal normalization technique. For example, the wave feature input module 802 may receive wave features selected from a signal normalized by dividing the signal with the mean of the signal and subtracted by a new signal mean of one.

The signal energy determination module 804 determines signal energy measurements for the wave features received by the wave feature input module 802. A signal energy measurement determined by the signal energy determination module 804 may be included as part of determined wave metric calculations for the wave features. The signal energy determination module 804 may determine a signal energy measurement using an applicable signal oscillatory energy measurement technique. Example signal oscillatory energy measurement techniques include one or a combination of skewness technique, kurtosis techniques, and measurements of an absolute deviation from a mean. Example Equation 1, shown below, illustrates an example technique of the signal energy determination module 804 determining signal energy measurements for the wave features.

$$E(s[t]) = \text{var}(s[t]) \quad \text{Example Equation 1}$$

In Example Equation 1, s[t] represents a signal window of the signal including one or a plurality of wave features for which wave metric calculations are determined. E represents a signal energy measurement determined by the signal energy determination module 804. Additionally, var represents a signal oscillatory energy measurement technique applied by the signal energy determination module 804 to determine the signal energy measurement E as a function of a specific signal window.

The signal mobility determination module 806 determines signal mobility measurements for the wave features received by the wave feature input module 802. A signal mobility measurement determined by the signal mobility determination module 806 may be included as part of determined wave metric calculations for the wave features. The signal mobility determination module 806 may determine a signal mobility measurement using an applicable technique for comparing oscillatory energy in the signal and its derivative. For example, the signal mobility determination module 806 may apply the Hjorth mobility parameter technique to determine signal mobility. Example Equation 2, shown below, illustrates an example of application of the Hjorth mobility parameter technique by the signal mobility determination module 806 for determining signal mobility measurements for the wave features.

$$M(s[t]) = \sqrt{\frac{E\left(\frac{ds}{dt}s[t]\right)}{E(s[t])}} \quad \text{Example Equation 2}$$

In Example Equation 2, E represents the signal energy measurements determined by the signal energy determination module 804, for example, according to Example Equation 1. M represents the signal mobility measurement as a function of the specific signal window. The signal mobility measurement as a function of the specific signal window is the square root of the signal energy measurement of the derivative of the specific signal window divided by the signal energy measurement of the specific signal window.

The signal complexity determination module 808 determines signal complexity measurements for the wave features received by the wave feature input module 802. A signal complexity measurement determined by the signal complexity determination module 808 may be included as part of determined wave metric calculations for the wave features. The signal complexity determination module 808 may determine a signal mobility measurement using an applicable technique for comparing oscillatory energy in the signal and second derivatives. For example, the signal complexity determination module 808 may apply the Hjorth complexity parameter technique to determine signal complexity. Example Equation 3, shown below, illustrates an example of application of the Hjorth complexity parameter technique by the signal complexity determination module 808 for determining signal complexity measurements for the wave features.

$$C(s[t]) = \sqrt{\frac{M\left(\frac{ds}{dt}s[t]\right)}{M(s[t])}} \quad \text{Example Equation 3}$$

In Example Equation 3, M represents the signal mobility measurements determined by the signal mobility determination module 806. Additionally, C represents the signal complexity measurement as a function of the specific signal window. The signal complexity measurement as a function of the specific signal window is the square root of the signal mobility measurement of the derivative of the specific signal window divided by the signal mobility measurement of the specific signal window.

The signal crossing rate determination module 810 determines signal crossing rate measurements for the wave features received by the wave feature input module 802. A signal crossing rate measurement, determined by the signal crossing rate determination module 810, may be included as part of determined wave metric calculations for the wave features. The signal crossing rate determination module 810 may determine a signal crossing rate measurement using an applicable technique for determining a crossing rate, with respect to a reference point, of a signal within a signal window. Example Equation 4, shown below, illustrates an example of application of an applicable technique for determining a signal crossing rate measurement by the signal crossing rate determination module 810 for the wave features.

$$Z(s[t]) = \frac{\sum_{t=0}^{T*F_s-1} \delta_{-sign(s[t])sign(s[t+1])}}{T} \quad \text{Example Equation 4}$$

The function illustrated in Example Equation 4 may be used by the signal crossing rate determination module 810 to determine a zero-crossing rate for the wave features. It is appreciated that the signal crossing rate determination module 810 may apply other functions to determining crossing rates with respect to other reference points. In Example Equation 4, Z represents the zero-crossing rate as a function of the specific signal window. Additionally, T represents the sampling interval, while $F_s$, represents the sampling frequency.

The signal non-oscillatory component determination module 812 determines signal non-oscillatory component measurements for the wave features received by the wave feature input module 802. A signal non-oscillatory component measurement determined by the signal non-oscillatory component determination module 812 may be included as part of determined wave metric calculations for the wave features. Example, signal non-oscillatory component measurements include a mean of a signal, a smoothed measure of the magnitude of non-oscillatory components of a signal, a median of a signal, and a mode of a signal. The signal non-oscillatory component determination module 812 may determine signal non-oscillatory component measurements using applicable technique for determining signal non-oscillatory component measurements.

In various embodiments, any of the signal energy determination module 804, the signal mobility determination module 806, the signal complexity determination module 808, the signal crossing rate determination module 810, and the signal non-oscillatory component determination module 812 may determine corresponding measurements included as part of wave metric calculations using wave features selected from a normalized signal. For example, signal energy measurements, signal mobility measurements, signal complexity measurements, signal crossing rate measurements, and signal non-oscillatory component measurements may be determined for wave features selected from a normalized signal.

The wave metric datastore 814 stores wave metric data indicating wave metrics determined for wave features by any of the signal energy determination module 804, the signal mobility determination module 806, the signal complexity determination module 808, the signal crossing rate determination module 810, and the signal non-oscillatory component determination module 812. For example, the wave metric datastore 814 may store wave metric data indicating signal energy measurements, signal mobility measurements, signal complexity measurements, signal crossing rate measurements, and signal non-oscillatory component measurements for selected wave features.

It will be understood that for some embodiments, the modules and datastores or the arrangement of modules and datastores may differ from what is depicted in FIG. 8.

Each of the modules and datastore of the wave metric calculation determination module 800 may be implemented using one or more digital devices. An example digital device is described regarding FIG. 5.

Figure 9:
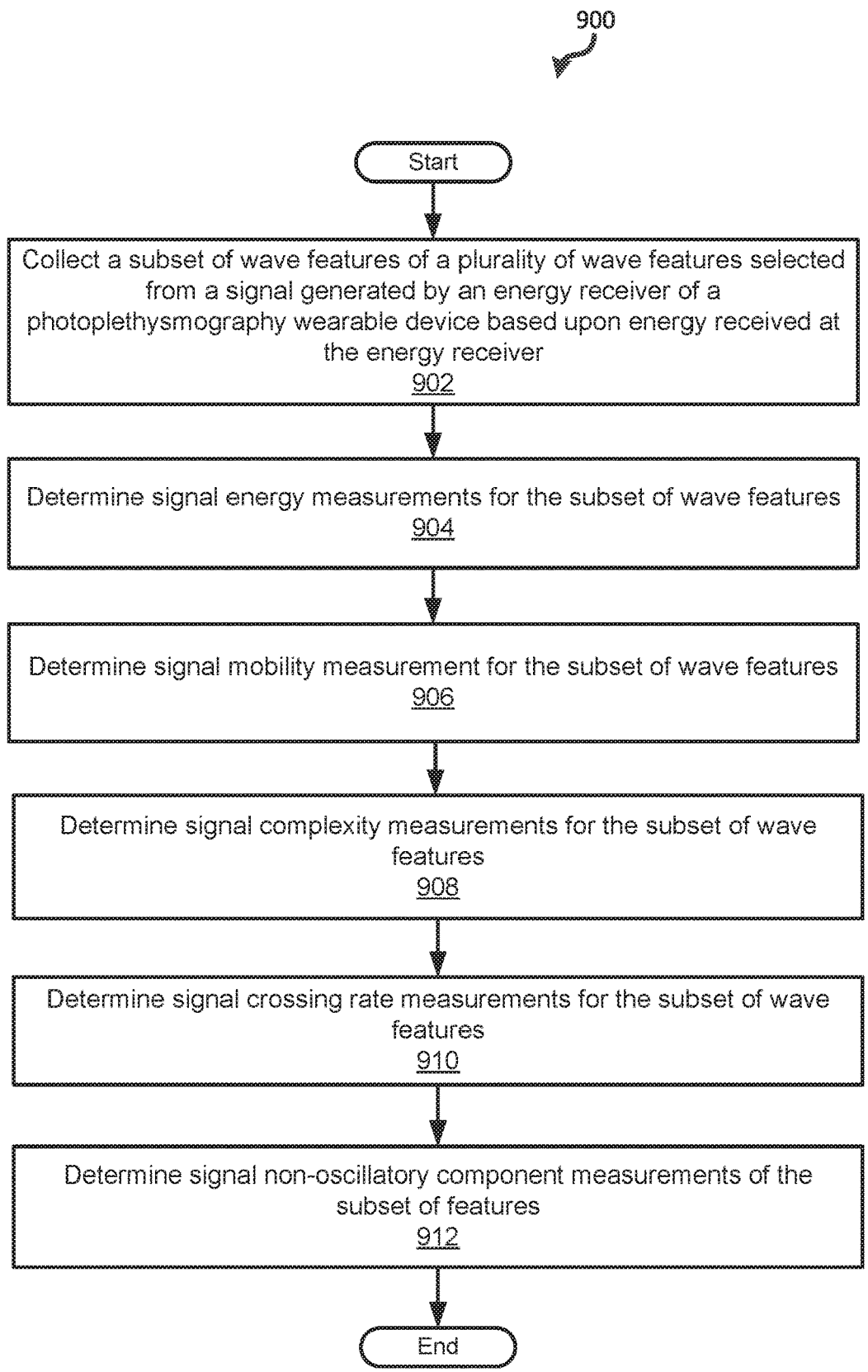
FIG. 9 depicts an example flow diagram of a method of determining wave metrics of a set of wave metrics for a subset of wave features.

FIG. 9 depicts an example flow diagram of a method 900 of determining wave metrics of a set of wave metrics for a subset of wave features. At step 902, the wave feature selection module 604 may collect a subset of wave features of a plurality of wave features selected from a signal generated by an energy receiver of a wearable photoplethysmography device 100 generated based upon energy received at the energy receiver are collected. Alternately, a wave feature input module may collect the subset of wave features of the plurality of wave features selected from a signal generated by an energy receiver of a wearable photoplethysmography device.

At step 904, the signal energy determination module 804 may determine signal energy measurements are determined for the subset of wave features. Signal energy measurements determined for the subset of wave features may be included as part of wave metric calculations used to determine validity of the signal for purposes of determining whether the wearable photoplethysmography device 100 is correctly positioned. Signal energy measurements may be determined using an applicable technique for measuring signal energy, such as one or a combination of skewness technique, kurtosis techniques, and measuring of an absolute deviation from a mean.

At step 906, the signal mobility determination module 806 determines signal mobility measurements for the subset of wave features. Signal mobility measurements determined for the subset of wave features may be included as part of wave metric calculations used to determine validity of the signal for purposes of determining whether the wearable photoplethysmography device 100 is correctly positioned. Signal mobility measurements may be determined using an applicable technique for measuring signal mobility, such as application of a Hjorth mobility parameter (e.g., see Example Equation 2). Alternately, signal mobility measurements may be determined using signal energy measurements determined at module 904.

At step 908, the signal complexity determination module 808 signal complexity measurements are determined for the subset of wave features. Signal complexity measurements determined for the subset of wave features may be included as part of wave metric calculations used to determine validity of the signal for purposes of determining whether the wearable photoplethysmography device 100 is correctly positioned. Signal complexity measurements may be determined using an applicable technique for measuring signal complexity, such as application of a Hjorth complexity parameter (e.g., see Example Equation 3). Additionally, signal complexity measurements may be determined using signal mobility measurements determined at module 906.

At step 910, the signal crossing rate measurements determination module 810 determines signal crossing rate measurements for the subset of wave features. Signal crossing rate measurements determined for the subset of wave features may be included as part of wave metric calculations used to determine validity of the signal for purposes of determining whether the wearable photoplethysmography device 100 is correctly positioned. Signal crossing rate measurements may be determined using an applicable technique for measuring signal crossing rates (e.g., see Example Equation 4). Additionally, signal complexity measurements may be determined using signal mobility measurements determined at module 906.

At step 912, the signal non-oscillatory component determination module 812 signal determines non-oscillatory components for the subset of wave features. Signal non-oscillatory components determined for the subset of wave features may be included as part of wave metric calculations used to determine validity of the signal for purposes of determining whether the wearable photoplethysmography device 100 is correctly positioned. Signal non-oscillatory components may be determined using an applicable technique for determining signal non-oscillatory components, such as calculating a mean of a signal.

Figure 10:
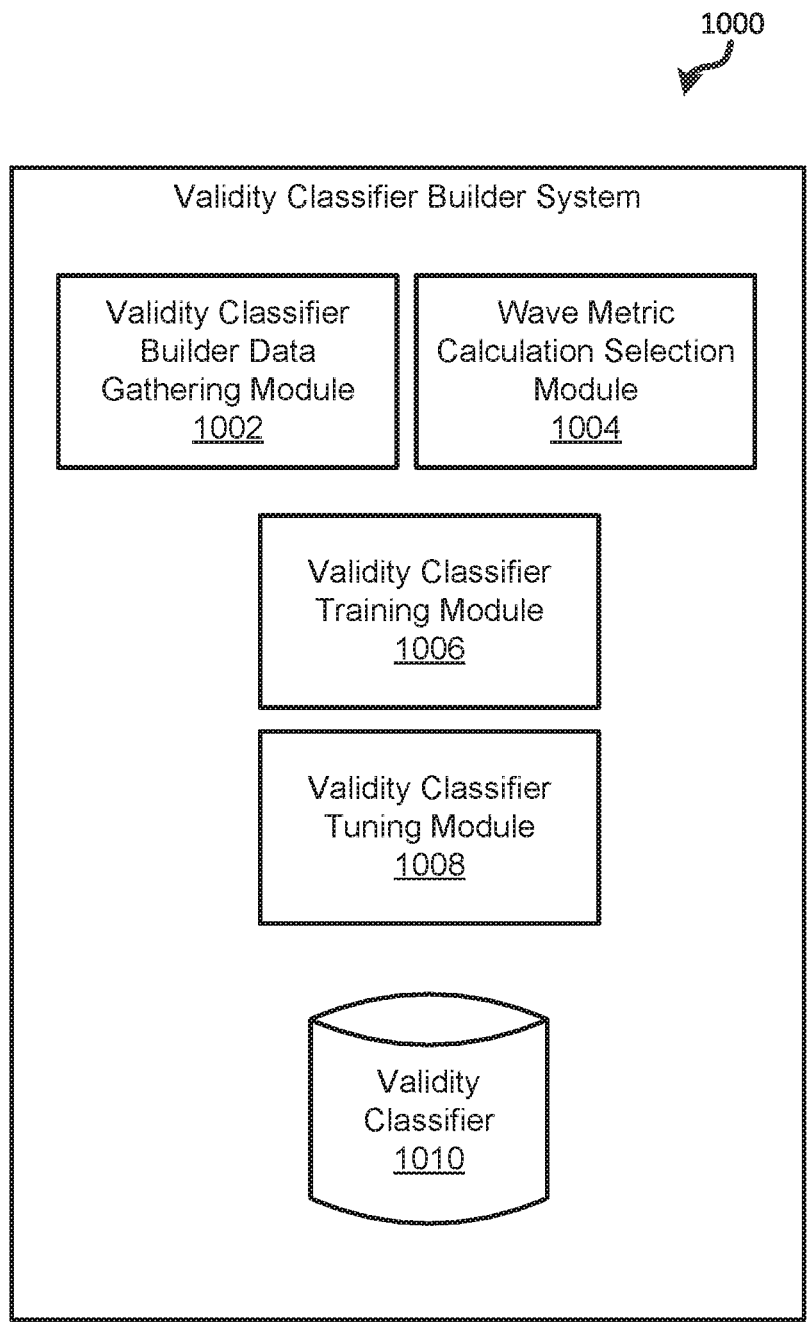
FIG. 10 is a block diagram of an example validity classifier builder system.

FIG. 10 is a block diagram of an example validity classifier builder system 1000. The validity classifier builder system 1000 generates a validity classifier used in determining validity of a signal for purposes of determining if a wearable photoplethysmography device is correctly positioned. In various embodiments, the validity classifier builder system 1000 is implemented remote from wearable photoplethysmography devices using the classifier for purposes of determining validity of signals received at the wearable photoplethysmography devices 100. For example, the validity classifier builder system 1000 may be remote from wearable photoplethysmography devices 100 and subsequently provide a generated validity classifier to the wearable photoplethysmography devices 100.

The validity classifier builder system 1000 includes a validity classifier builder data gathering module 1002, a wave metric calculation selection module 1004, a validity classifier training module 1006, a validity classifier tuning module 1008, and a validity classifier datastore 1010.

The validity classifier builder data gathering module 1002 gathers data used in building a validity classifier for purposes of determining whether signals received by a wearable photoplethysmography device are valid. The validity classifier builder data gathering module 1002 may receive signals generated by one or a plurality of wearable photoplethysmography device. Signals received by the validity classifier builder data gathering module 1002 may include signals generated by one or a plurality of wearable photoplethysmography devices 100 in operation to measure medical signs. For example, the validity classifier builder data gathering module 1002 may receive signals generated by energy receivers of wearable photoplethysmography devices 100 in response to absorbed energy at the energy receivers. The validity classifier builder data gathering module 1002 receives signals from an energy receiver and/or an energy transmitter of a wearable photoplethysmography device 100 at a sampling rate of 15 Hz. Additionally, the validity classifier builder data gathering module 10002 may filter, e.g. using a low-pass filter, received signals.

In various embodiments, the validity classifier builder data gathering module 1002 may receive indications of whether signals received from wearable photoplethysmography devices 100 are valid or invalid, according to whether or not the wearable photoplethysmography devices 100 are correctly positioned in operation. Specifically, the validity classifier builder data gathering module 1002 may receive indications specifying that signals received from a specific wearable photoplethysmography device 100 are generated when the device is either positioned correctly in operation, being worn but not positioned correctly, or not being worn at all.

For example, the validity classifier builder data gathering module 1002 may receive input indicating signal validity data specifying a wearable photoplethysmography device 100 providing signals is positioned properly on a wrist, finger, or thumb of a user, while the user is stationary or walking on a treadmill. In another example, the validity classifier builder data gathering module 1002 may receive input indicating signal invalidity data specifying a wearable photoplethysmography device 100 providing signals is located indoors, outdoors, in a dark environment, in a light environment, while a user is walking, tapping, covering, or uncovering energy receivers or transmitters of the device, or the user is facing energy emission sources (e.g. LCD videos).

In various implementations, the validity classifier builder data gathering module 1002 may receive alternating invalid and valid signals from a wearable photoplethysmography device 100. For example, the validity classifier builder data gathering module 1002 may receive invalid signals for a minute and receive valid signals for a minute in an alternating fashion.

In various implementations, the validity classifier builder data gathering module 1002 may build valid and invalid data sample collections based on signals received from wearable photoplethysmography devices 100. Valid and invalid data sample collections include samples of known invalid and valid signals within specific signal windows. For example, the validity classifier builder data gathering module 1002 may build valid and invalid data sample collections including samples of 8 second signal windows of known valid and invalid signals received from wearable photoplethysmography devices 100. In another example, the validity classifier builder data gathering module 1002 may build valid and invalid data sample collections that in combination contain over a large number of (e.g., 12,000) sampled of valid and invalid signals received from wearable photoplethysmography devices 100.

The wave metric calculation selection module 1004 selects wave metric calculations. Wave metric calculations selected by the wave metric calculation selection module 1004 may be determined from signals received by the validity classifier builder data gathering module 1002 for use in building a validity classifier. The metric wave calculation selection module 1004 may select wave metric calculations from the list of wave metric calculations as discussed with respect to FIG. 1. For example, the wave metric calculation selection module 1004 may select a set of wave metric calculations to determine from the signals received by the validity classifier builder data gathering module 1002 including signal energy measurements, signal mobility measurements, signal complexity measurements, signal crossing rate measurements, and signal non-oscillatory component measurements. Further in the example, the wave calculation selection module 1004 selects the set of wave metric calculations because they may be calculated in a time directly proportional to a length of a received signal and/or a validity classifier created from the calculations may yield a simple polynomial for validity prediction.

In one implementation, the wave metric calculation selection module 1004 may systematically add or remove wave metric calculations to or from selected wave metric calculations. The wave metric calculation selection module 1004 may systematically add or remove wave metric calculations to or from selected wave matric calculations based on accuracy performance in determining validity of a signal using a generated validity classifier. Additionally, the wave metric calculation selection module 1004 may systematically add or remove wave metric calculations to or form selected wave metric calculations based on computational costs associated with determining the wave metric calculations.

The validity classifier training module 1006 determines wave metric calculations for signals received by the validity classifier builder data gathering module. For example, the validity classifier training module 1006 may determine wave metric calculations for any number of the valid and invalid data samples of the valid and invalid data sample collections generated by the validity classifier builder data gathering module 1002. The validity classifier training module 1006 may determine a set of wave metric calculations as selected by the wave metric calculation selection module 1004. For example, the validity classifier training module 1006 may determine signal energy measurements, signal mobility measurements, signal complexity measurements, signal crossing rate measurements, and signal non-oscillatory component measurements for any number of the valid and invalid data samples in the valid and invalid data sample collections. Further in the example, the validity classifier training module 1006 may determine the measurements according to the techniques described with reference to the wave metric calculation determination module 800 (e.g. as illustrated by Example Equations 1-4).

The validity classifier training module 1006 builds a validity classifier by training the validity classifier. In training a validity classifier, the validity classifier training module may analyze patterns of wave metric calculations of known valid and invalid signals. In analyzing patters of wave metric calculations in building a validity classifier, the validity classifier training module 1006 may apply one or a combination of applicable machine learning algorithms to the wave metric calculations determined by the validity classifier training module 1006. In applying applicable machine learning algorithms or pattern recognitions algorithms to the wave metric calculations, the validity classifier training module 1006 may segment determined wave metric calculations of known valid and invalid signals into clusters of wave metric calculations of known valid and invalid signals. Further, the validity classifier training module 1006 may generate and segment validity scores generated from determined wave metric calculations and associated with known valid and invalid signals into clusters of validity scores of known valid and invalid signals. Example algorithms the validity classifier training module 1006 may apply in building the validity classifier include kernel method algorithms, non-linear kernel method algorithms, polynomial kernel method algorithms, Gaussian kernels, or radial-bases kernels.

In various embodiments, the validity classifier training module 1006 may apply a quadratic kernel in segmenting wave metric calculations into clusters of wave metric calculations of known valid and invalid signals. Example Equation 5, shown below, illustrates an example of a quadratic kernel equation the validity classifier training module 1006 may use in building the validity classifier.

$$K(x_1, x_2) = (x_1^T x_2 + 1)^p \text{ where } p = 2 \qquad \text{Example Equation 5}$$

In Example Equation 5, x1 and x2 are vectors representing the determined wave metric calculations of known valid and invalid signals. The kernel equation shown in Example Equation 5 may be used to process a dot product of vectors representing the determined wave metric calculations in a high dimensional space without explicitly making the combination of the vectors. For example, If $x_1=(a, b)$ and $x_2=(c, d)$ in the kernel equation above, the output is $K(x_1,x_2)=1+a^2b^2+2abcd+c^2d^2+2ab+2cd$, which may also be broken into a dot product between vectors containing various powers and coefficients on the variables, $(1, a^2, \sqrt{2}ab, b^2, \sqrt{2}a, \sqrt{2}b)\cdot(1, c^2, \sqrt{2}cd, d^2, \sqrt{2}c, \sqrt{2}d)$.

In various embodiments, the output of the application of an applicable machine learning algorithm to the determined wave metric calculations (e.g. Example Equation 5), is substituted into an applicable support vector machine. Example Equation 6, shown below, illustrates an example support vector machine.

$$F(x) = \text{sign}\Big(\sum_i a_i y_i K(x_i, x) + b\Big) \qquad \text{Example Equation 6}$$

In Example Equation 6, $K(x_i,x)$ is the output of the kernel equation applied to the determined wave metric calculations, where $x_i$ may serve as the training input (e.g. wave metric calculations of known valid and invalid signals, and x may serve as unlabeled input). A support vector machine forms the basis of the validity classifier and is used in generating, at least in part, validity scores for signals of unknown validity. In various embodiments, determined wave metric calculations may be input into the support vector machine to determine a validity score for a signal of unknown validity. For example, the signal validity classification system or may input determined wave metric calculations into the support vector machine generated from application of an applicable machine learning algorithm to wave metric calculations of known valid and invalid signals, to determine whether a signal of unknown validity is actually valid. With reference to the Example Equation 6, x serves as an unlabeled input in which determined wave metric calculations from signals of unknown validity may be input to calculate, at least in part, a validity score for the signals.

The validity classifier tuning module 1008 tunes the validity classifier trained, or otherwise generated, by the validity classifier training module 1006. In various embodiments, in tuning a validity classifier trained by the validity classifier training module 1006, the validity classifier tuning module 1008 may fit the classifier to a logistic function. For example, validity classifier tuning module 1008 may fit a support vector machine used to generate validity scores for signals based on determined wave metric calculations to a logistic function. Example Equation 7, shown below, illustrates an example of a classifier fit to a logistic functions.

$$\text{Valid Probability (score)} = \frac{1}{1 + e^{-a*score-b}} \qquad \text{Example Equation 7}$$

In Example Equation 6, the score may be generated through application of wave metric calculations to a support vector machine (e.g., as shown in Example Equation 6), as part of generating a validity score for a signal through application of the validity classifier. In Example Equation 7, a and b serve as fit parameters and are used to fit output validity scores generated through application Equation 7 within one or a plurality of specific ranges.

In various embodiments, the validity classifier tuning module 1008 may set a validity threshold, included as part of or otherwise associated with the validity classifier. The validity classifier tuning module 1008 may set a validity threshold for the validity classifier to achieve a specific number of true positive results for determining signal validity. For example, the validity classifier tuning module 1008 may set a validity threshold to achieve a true positive result determination rate of 99%. Additionally, the validity classifier tuning module 1008 may set a validity threshold of a validity classifier specific to and/or based on one or a combination of a device type of a photoplethysmography device 100 using the validity classifier, medical signs being measured by a photoplethysmography device 100 using the validity classifier, and characteristics of a user of a photoplethysmography device 100 using the validity classifier. For example, if clusters of valid and invalid validity scores, determined through application of the validity classifier, differ for different types of photoplethysmography devices 100, then the validity classifier tuning module 1008 may set two different validity thresholds to use dependent on which device type is being used.

The validity classifier datastore 1010 stores validity classifier data indicating a validity classifier generated by the validity classifier training module 1006 and/or tuned by the validity classifier tuning module 1008. For example, validity classifier data stored in the validity classifier datastore 1010 may include a support vector machine trained using wave metric calculations of known valid and invalid signals and fit to a logistic function to generate validity scores falling within one or a plurality of specific ranges. Additionally, validity classifier data stored in the validity classifier datastore 1010 may include one or a validity of thresholds to use in determining whether signals are valid through application of validity classifiers. In various embodiments, the validity classifier datastore 1010 may include indications of when to use specific validity thresholds. For example, validity classifier data stored in the validity classifier datastore 1010 may indicate which validity thresholds to use to achieve a specific number of true positive results, and which validity thresholds to use based on device type of photoplethysmography devices 100, user characteristics of users of photoplethysmography devices 100, and medical signs measured by photoplethysmography devices 100. A validity threshold used in application of the validity classifier may be adjusted to one of a plurality of validity thresholds using validity classifier data stored in the validity classifier datastore 1010.

It will be understood that for some embodiments, the modules and datastores or the arrangement of modules and datastores may differ from what is depicted in FIG. 10.

Each of the modules and datastore of the validity classifier builder system 1000 may be implemented using one or more digital devices. An example digital device is described regarding FIG. 5.

Figure 11:
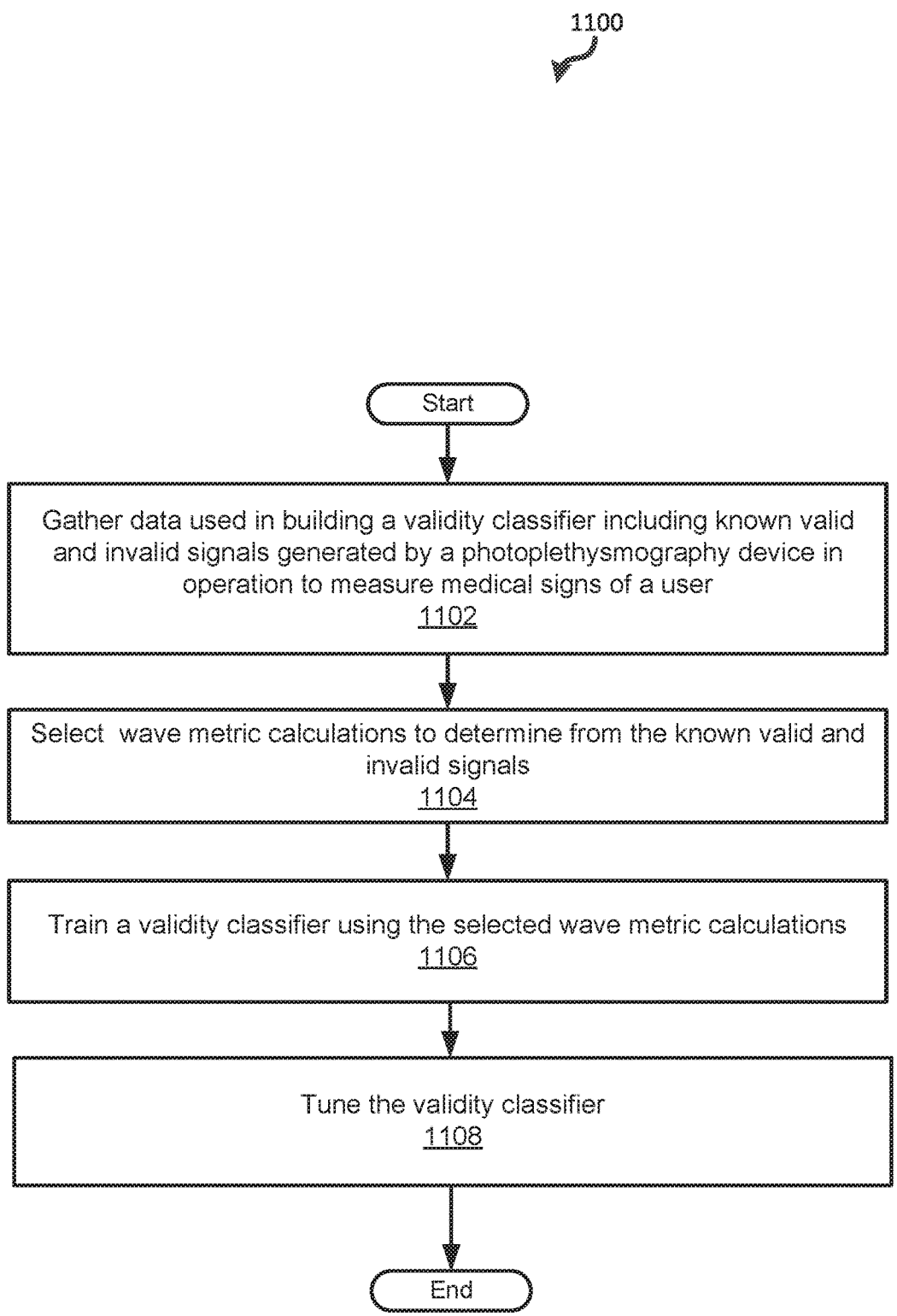
FIG. 11 depicts an example flow diagram of a method of generating a validity classifier for purposes of determining whether a wearable photoplethysmography device is correctly positioned in operating to measure medical signs of a user.

FIG. 11 depicts an example flow diagram of a method 1100 of generating a validity classifier for purposes of determining whether a wearable photoplethysmography device 100 is correctly positioned in operating to measure medical signs of a user. At step 1102, data used in building a validity classifier including known valid and invalid signal is gathered. Data gathered at step 1102 includes signals generated by a wearable photoplethysmography device in operating to measure medical signs of a user. Data gathered at step 1102 may be gathered by a validity classifier builder data gathering module 1002. Data gathered at step 1102 may include signal validity data indicating whether a wearable photoplethysmography device 100 is correctly positioned. Additionally, data gathered at step 1102 may include signal invalidity data indicating a wearable photoplethysmography device is incorrectly positioned or operating in an environment leading to receiving invalid signal.

At step 1104, wave metric calculations are selected to determine from the known valid and invalid signals. Wave metric calculations may be selected by the wave metric calculation selection module 1004. Potential wave metric calculations capable of being selected include the wave metric calculation in the list of wave metric calculations as discussed with respect to FIG. 1. For example, set of wave metric calculations including signal energy measurements, signal mobility measurements, signal complexity measurements, signal crossing rate measurements, and signal non-oscillatory component measurements may be selected. Wave metric calculations may be selected based on either or both an accuracy performance in determining validity of signals using the wave metric calculations and computational costs of determining the wave metric calculations.

At step 1106, a validity classifier is trained using the selected wave metric calculations. The validity classifier training module 1006 may train a validity classifier using the selected wave metric calculations. In training a validity classifier an applicable machine learning algorithm may be applied wave metric calculations of the selected wave metric calculations determined from the known valid and invalid signals. For example, a kernel equation may be applied to wave metric calculations of the selected wave metric calculations. Additionally, output of applying a machine learning algorithm to wave metric calculations of the known valid and invalid signals may be applied to a support vector machine as training input to form the validity classifier. For example, output of a kernel equation applied to wave metric calculations of the selected wave metric calculations may be applied as training input to a support vector machine.

At step 1108, the validity classifier is tuned to produce validity scores within one or a plurality of specific ranges. The validity classifier tuning module 1008 may tune to the classifier to produce validity scores within one or a plurality of specific ranges. For example, a logistic function may be fit to the validity classifier to cause scores generated through application of the validity classifier to fall within one or a plurality of specific ranges.

At step 1108, in various embodiments, in tuning the validity classifier, one or a plurality of validity thresholds are determined for the validity classifier. The validity classifier tuning module 1008 may select one or a plurality of validity thresholds as part of tuning the validity classifier. Validity thresholds may be selected to achieve a specific true positive result determination rate. For example a validity threshold may be selected to achieve a 99% true positive result determination rate. Additionally, validity thresholds may be selected according to one or a combination of device type of photoplethysmography devices 100, user characteristics of users of photoplethysmography devices 100, and medical signs measured by photoplethysmography devices 100.

The present invention(s) are described above with reference to example embodiments. It will be apparent to those skilled in the art that various modifications may be made and other embodiments may be used without departing from the broader scope of the present invention(s). Therefore, these and other variations upon the example embodiments are intended to be covered by the present invention(s).

The invention claimed is:

1. A wrist-worn wearable photoplethysmography (PPG) device, comprising:
   an energy transmitter disposed in the wrist-worn wearable photoplethysmography device configured to project energy towards a wrist of a user;

an energy receiver disposed in the wrist-worn wearable photoplethysmography device configured to generate a user PPG signal based on the energy received at the energy receiver; and a processor operatively connected to the energy receiver and the energy transmitter, the processor configured to:

determine wave features from the user PPG signal based on at least a portion of the projected energy transmitted from the energy transmitter;

determine wave metric calculations of a set of wave metric calculations for the wave features;

classify the user PPG signal by applying a validity classifier to at least one of the wave metric calculations to generate a validity score for the user PPG signal, wherein the validity classifier is configured to generate the validity score by receiving training wave metric calculations for known valid and known invalid signals, wherein the training wave metric calculations comprises one or more signal energy measurements, generating training validity scores corresponding to the known valid and known invalid signals, and generating the validity score for the user PPG signal based on the training validity scores for the known valid and known invalid signals; and determine, based on the validity score and a validity threshold, whether the wearable photoplethysmography device is correctly positioned on the user, wherein the processor is further configured to one or more of stop operation, operate in a reduced capacity, or deactivate one or more components of the wrist-worn wearable PPG device when it is determined that the wrist-worn wearable PPG device is not correctly positioned based on a comparison of the validity score to the validity threshold.

2. The wearable photoplethysmography device of claim 1, wherein the wrist-worn device comprises a central unit, a sensory array coupled to the central unit and comprising at least the energy transmitter and the energy receiver, and a display mounted on the central unit.

3. The wearable photoplethysmography device of claim 1, wherein the device is a bracelet.

4. The wearable photoplethysmography device of claim 1, wherein the wave metric calculations
of the set of wave metric calculations comprise signal energy measurements of the user PPG signal determined from the wave features.

5. The wearable photoplethysmography device of claim 4, wherein the wave metric calculations of the set of wave metric calculations comprise signal mobility measurements of the user PPG signal determined from the wave features and the signal energy measurements of the user PPG signal determined from the wave features.

6. The wearable photoplethysmography device of claim 5, wherein the wave metric calculations of the set of wave metric calculations comprise signal complexity measurements of the user PPG signal determined from the wave features and the signal mobility measurements of the user PPG signal determined from the wave features.

7. The wearable photoplethysmography device of claim 1, wherein the wave metric calculations of the set of wave metric calculations comprise one or a combination of signal crossing measurements of the user PPG signal and signal non- oscillatory component measurements of the user PPG signal determined from the wave features.

8. The wearable photoplethysmography device of claim 1, wherein the validity classifier is generated from one or a combination of signal energy measurements, signal mobility measurements, signal complexity measurements, signal crossing measurements, and signal non-oscillatory component measurements of signals known to be valid or invalid by being generated by at least one wearable photoplethysmography device correctly positioned in operating to measure medical signs and at least another wearable photoplethysmography device incorrectly positioned in operating to measure the medical signs.

9. The wearable photoplethysmography device of claim 1, wherein the processor is further configured to:

determine whether the wearable photoplethysmography device is operating to measure medical signs of the user based on a comparison of the validity score to the validity threshold; and cause the energy transmitter to stop operating in emitting energy for use by the wearable photoplethysmography device in operating to measure the medical signs of the user.

10. The wearable photoplethysmography device of claim 1, wherein the validity threshold is pre-set to achieve a specific number of true positive results in determining whether the user PPG signal generated by the energy receiver is actually valid.

11. The wearable photoplethysmography device of claim 1, wherein the validity threshold is pre-set based on one or a combination of a device type of the wearable photoplethysmography device, medical signs being measured by the photoplethysmography device, characteristics of the user of the photoplethysmography device, or a desired rate of achieving true positive results.

12. A system for determining positioning of a wrist-worn wearable photoplethysmography (PPG) device on a user, comprising:

the wrist-worn wearable photoplethysmography device comprising:

an energy transmitter disposed in the wrist-worn wearable photoplethysmography device configured to project energy towards a wrist of the user;

an energy receiver disposed in the wrist-worn wearable photoplethysmography device configured to generate a user PPG signal based on the energy received at the energy receiver;

communication circuitry; and a processor operatively connected to the energy transmitter, the energy receiver, and the communication circuitry; and a server in communication with the wearable photoplethysmography device, wherein the processor is configured to:

determine wave features from the user PPG signal based on at least a portion of the projected energy transmitted from the energy transmitter;

determine wave metric calculations of a set of wave metric calculations for the wave features;

classify the signal by applying a validity classifier to at least one of the wave metric calculations to generate a validity score for the user PPG signal, wherein the validity classifier is configured to generate the validity score by receiving training wave metric calculations for known valid and known invalid signals, wherein the training wave metric calculations comprises one or more signal energy measurements, generating training validity scores corresponding to the known valid and known invalid signals, and generating the validity score for the user PPG signal based on the training validity scores for the known valid and known invalid signals;

determine, based on the validity score and a validity threshold, whether the wearable photoplethysmography device is correctly positioned on the user, wherein the processor is further configured to one or more of stop operation, operate in a reduced capacity, or deactivate one or more components of the wrist-worn wearable PPG device when it is determined that the wrist-worn wearable PPG device is not correctly positioned based on a comparison of the validity score to the validity threshold.

13. The system of claim 12, wherein the wearable photoplethysmography device is a bracelet.

14. The system of claim 12, wherein the wave metric calculations of the set of wave metric calculations comprise signal energy measurements of the user PPG signal determined from the wave features.

15. The system of claim 14, wherein the wave metric calculations of the set of wave metric calculations comprise signal mobility measurements of the user PPG signal determined from the wave features and the signal energy measurements of the user PPG signal determined from the wave features.

16. The system of claim 12, wherein the validity threshold is pre-set to achieve a specific number of true positive results in determining whether the user PPG signal generated by the energy receiver is actually valid.

17. The system of claim 12, wherein the validity threshold is pre-set based on one or a combination of a device type of the wearable photoplethysmography device, medical signs being measured by the photoplethysmography device, characteristics of the user of the photoplethysmography device, or a desired rate of achieving true positive results.

* * * * *

UNITED STATES PATENT AND TRADEMARK OFFICE
CERTIFICATE OF CORRECTION

Page 1 of 2

PATENT NO. : 12,004,879 B2
APPLICATION NO. : 17/648498
DATED : June 11, 2024
INVENTOR(S) : Elad Ferber et al.

It is certified that error appears in the above-identified patent and that said Letters Patent is hereby corrected as shown below:

In the Specification

Column 2, Line 45, delete "signal;" and insert -- signal. --

Column 2, Line 49, delete "score;" and insert -- score. --

Column 2, Line 52, delete "to the to the" and insert -- to the --

Column 2, Line 54, delete "user;" and insert -- user. --

Column 3, Line 34, delete "to the to the" and insert -- to the --

Column 29, Lines 12-14, delete "$\sum_{t=0}^{T*Fs-1} \delta - sign(s[t])sign(s[t+1])$ $T$" and insert -- $\frac{\sum_{t=0}^{T*Fs-1} \delta - sign(s[t]),sign(s[t+1])}{T}$ --

Column 29, Line 25, delete "$F_s$," and insert -- $F_s$ --

Column 32, Line 63, delete "matric" and insert -- metric --

Column 33, Line 59, delete "$(x_1^T x_2 + 1)^p$" and insert -- $(x_1^T x_2 + 1)^p,$ --

Column 34, Line 1, delete "If" and insert -- if --

Signed and Sealed this
Twenty-eighth Day of January, 2025

Coke Morgan Stewart
*Acting Director of the United States Patent and Trademark Office*

In the Claims

Column 37, Line 66, Claim 7, delete "non- oscillatory" and insert -- non-oscillatory --

Column 39, Line 5, Claim 12, after "signals;" insert -- and --